US007759303B2

(12) United States Patent
Seong et al.

(10) Patent No.: US 7,759,303 B2

(45) Date of Patent: Jul. 20, 2010

(54) METHOD FOR IMPROVING SOLUBILITY AND FOLDING EFFICIENCY OF TARGET PROTEINS USING RNA AS MOLECULAR CHAPERONE

(75) Inventors: Baik Lin Seong, Seoul (KR); Seong-Il Choi, Seoul (KR); Hang Cheol Shin, Seoul (KR); Ki-Sun Ryu, Seoul (KR); Kyoung Sim Han, Gyeonggi-do (KR); Chul Woo Kim, Seoul (KR); Byung Hee Kim, Gyeongsangnam-do (KR)

(73) Assignee: Biotrion Co., Ltd., Seongnam-Si, Gyeonggi-Do (KR)

( * ) Notice: Subject to any disclaimer, the term of this patent is extended or adjusted under 35 U.S.C. 154(b) by 0 days.

(21) Appl. No.: 11/482,401

(22) Filed: Jul. 7, 2006

(65) Prior Publication Data

US 2006/0292667 A1 Dec. 28, 2006

Related U.S. Application Data

(63) Continuation-in-part of application No. 10/371,771, filed on Feb. 21, 2003, now abandoned.

(30) Foreign Application Priority Data

Aug. 19, 2002 (KR) .......................... 2002-0048929

(51) Int. Cl.

| | |
|---|---|
| ***C07K 14/00*** | (2006.01) |
| ***C07H 21/02*** | (2006.01) |
| ***C12N 15/00*** | (2006.01) |

(52) U.S. Cl. .......................... 514/2; 530/300; 536/23.1; 435/69.7

(58) Field of Classification Search ....................... None
See application file for complete search history.

(56) References Cited

OTHER PUBLICATIONS

Bach, et al., *Escherichia coli* maltose-binding protein as a molecular chaperone for recombinant intracellular cytoplasmic single-chain antibodies, Journal of Molecular Biology, 2001, 312:79-93.

Davis, et al., New fusion protein systems designed to give soluble expression in *Escherichia coli*, Biotechnology and Bioengineering, 1999, 65(4):382-388.

Sulijoadikusmo, et al., Another function for the mitochondrial ribosomal RNA: protein folding, Biochemistry, 2001, 40:11559-11564.

Commans, et al., Solution structure of the anticodon-binding domain of *Escherichia coli* Lysyl-tRNA synthetase and studies of its interaction with tRNA Lys, 1995, 253:100-113.

Elton, et al., Identification of amino acid residues of influenza virus nucleoprotein essential for RNA binding, Journal of Virology, 1999, 73(9):7357-7367.

*Primary Examiner*—Anand U Desai
(74) *Attorney, Agent, or Firm*—Lucas & Mercanti, LLP

(57) ABSTRACT

Disclosed is a method for improving folding efficiency and solubility of a target protein linked to a RNA-binding protein by using RNA molecule as a molecular chaperone, wherein the RNA molecule interacts with the RNA-binding protein. More particularly, the present invention discloses method for improving folding efficiency and solubility of a target protein by transformation of a host cell with a expression vector comprising a polynucleotide encoding the target protein linked to an RNA-binding protein; culturing the transformed host cell in an appropriate culture medium under the condition that an RNA molecule either resident inside the host cell or provided by cotransformation of the host cell with polynucleotide encoding the RNA molecule interacts with the RNA-binding protein; and purifying the soluble protein from host cell lysate. The method of the present invention is very useful for production of soluble proteins for therapeutic, prophylactic and diagnostic applications.

11 Claims, 22 Drawing Sheets a marker RS RS-PHM b a b

SEQUENCE LISTING

```
<160> NUMBER OF SEQ ID NOS: 60

<210> SEQ ID NO 1
<211> LENGTH: 35
<212> TYPE: DNA
<213> ORGANISM: Artificial Sequence
<220> FEATURE:
<223> OTHER INFORMATION: forward primer for lysyl tRNA synthetase

<400> SEQUENCE: 1

gactaccata tgtctgaaaa cacgcacagg gcgct                              35


<210> SEQ ID NO 2
<211> LENGTH: 78
```

-continued

<212> TYPE: DNA
<213> ORGANISM: Artificial Sequence
<220> FEATURE:
<223> OTHER INFORMATION: reverse primer for lysyl tRNA synthetase

<400> SEQUENCE: 2
gactccaagc ttgtcgacga tatcggatcc ggtacccttg tcatcgtcat cttttaccgg 60
acgcatcgcc gggaacag 78

<210> SEQ ID NO 3
<211> LENGTH: 40
<212> TYPE: DNA
<213> ORGANISM: Artificial Sequence
<220> FEATURE:
<223> OTHER INFORMATION: forward primer for tyrosyl tRNA synthetase

<400> SEQUENCE: 3
gtcatccata tggcaagcag taacttgatt aaacaattgc 40

<210> SEQ ID NO 4
<211> LENGTH: 46
<212> TYPE: DNA
<213> ORGANISM: Artificial Sequence
<220> FEATURE:
<223> OTHER INFORMATION: reverse primer for tyrosyl tRNA synthetase

<400> SEQUENCE: 4
gactacggta cctttccagc aaatcagaca gtaattcttt ttaccg 46

<210> SEQ ID NO 5
<211> LENGTH: 36
<212> TYPE: DNA
<213> ORGANISM: Artificial Sequence
<220> FEATURE:
<223> OTHER INFORMATION: forward primer for tryptophan tRNA synthetase

<400> SEQUENCE: 5
gtcatccata tgactaagcc catcgttttt agtggc 36

<210> SEQ ID NO 6
<211> LENGTH: 36
<212> TYPE: DNA
<213> ORGANISM: Artificial Sequence
<220> FEATURE:
<223> OTHER INFORMATION: reverse primer for tryptophan tRNA synthetase

<400> SEQUENCE: 6
gtcatcggat ccacgcttcg ccacaaaacc aatcgc 36

<210> SEQ ID NO 7
<211> LENGTH: 33
<212> TYPE: DNA
<213> ORGANISM: Artificial Sequence
<220> FEATURE:
<223> OTHER INFORMATION: forward primer for S1

<400> SEQUENCE: 7
gtcatccata tgactgaatc ttttgctcaa ctc 33

<210> SEQ ID NO 8
<211> LENGTH: 36
<212> TYPE: DNA
<213> ORGANISM: Artificial Sequence
<220> FEATURE:
<223> OTHER INFORMATION: reverse primer for S1

<400> SEQUENCE: 8
gtcatcggat ccctcgcctt tagctgcttt gaaagc 36

<210> SEQ ID NO 9
<211> LENGTH: 30
<212> TYPE: DNA
<213> ORGANISM: Artificial Sequence
<220> FEATURE:
<223> OTHER INFORMATION: forward primer for S4

<400> SEQUENCE: 9
gtcatccata tgcagggttc tgtgacagag 30

<210> SEQ ID NO 10
<211> LENGTH: 33
<212> TYPE: DNA
<213> ORGANISM: Artificial Sequence
<220> FEATURE:
<223> OTHER INFORMATION: reverse primer for S4

<400> SEQUENCE: 10
gtcatcggat ccaattcggg tagaagccgg cac 33

<210> SEQ ID NO 11
<211> LENGTH: 33
<212> TYPE: DNA
<213> ORGANISM: Artificial Sequence
<220> FEATURE:
<223> OTHER INFORMATION: forward primer for S17

<400> SEQUENCE: 11
gtcatccata tgaccgataa aatccgtact ctg 33

<210> SEQ ID NO 12
<211> LENGTH: 33
<212> TYPE: DNA
<213> ORGANISM: Artificial Sequence
<220> FEATURE:
<223> OTHER INFORMATION: reverse primer for S17

<400> SEQUENCE: 12
gtcatcggat cccagaaccg ctttctctac aac 33

<210> SEQ ID NO 13
<211> LENGTH: 21
<212> TYPE: DNA
<213> ORGANISM: Artificial Sequence
<220> FEATURE:
<223> OTHER INFORMATION: forward primer for Hsp15

<400> SEQUENCE: 13
gtcatccata tgaaagagaa a 21

<210> SEQ ID NO 14
<211> LENGTH: 36
<212> TYPE: DNA
<213> ORGANISM: Artificial Sequence
<220> FEATURE:
<223> OTHER INFORMATION: reverse primer for Hsp15

<400> SEQUENCE: 14
gtcatcggat ccttcactgt cgccgtgttt aaatcg 36

<210> SEQ ID NO 15
<211> LENGTH: 30

-continued

```
<212> TYPE: DNA
<213> ORGANISM: Artificial Sequence
<220> FEATURE:
<223> OTHER INFORMATION: forward primer for DbpA

<400> SEQUENCE: 15

gtcatccata tgacgccggt gcaggccgcc                                        30


<210> SEQ ID NO 16
<211> LENGTH: 32
<212> TYPE: DNA
<213> ORGANISM: Artificial Sequence
<220> FEATURE:
<223> OTHER INFORMATION: reverse primer for DbpA

<400> SEQUENCE: 16

gtcatcggat ccttttaata accgcacccg gc                                     32


<210> SEQ ID NO 17
<211> LENGTH: 32
<212> TYPE: DNA
<213> ORGANISM: Artificial Sequence
<220> FEATURE:
<223> OTHER INFORMATION: forward primer for Ffh

<400> SEQUENCE: 17

gtcatccata tgtttgataa tttaaccgat cg                                     32


<210> SEQ ID NO 18
<211> LENGTH: 30
<212> TYPE: DNA
<213> ORGANISM: Artificial Sequence
<220> FEATURE:
<223> OTHER INFORMATION: reverse primer for Ffh

<400> SEQUENCE: 18

gtcatcggat ccgcgaccag ggaagcctgg                                        30


<210> SEQ ID NO 19
<211> LENGTH: 36
<212> TYPE: DNA
<213> ORGANISM: Artificial Sequence
<220> FEATURE:
<223> OTHER INFORMATION: forward primer for c5

<400> SEQUENCE: 19

gtcatccata tggttaagct cgcatttccc agggag                                 36


<210> SEQ ID NO 20
<211> LENGTH: 32
<212> TYPE: DNA
<213> ORGANISM: Artificial Sequence
<220> FEATURE:
<223> OTHER INFORMATION: reverse primer for C5

<400> SEQUENCE: 20

gtcatcggat ccggacccgc gagccaggcg ac                                     32


<210> SEQ ID NO 21
<211> LENGTH: 41
<212> TYPE: DNA
<213> ORGANISM: Artificial Sequence
<220> FEATURE:
<223> OTHER INFORMATION: forward primer for NP

<400> SEQUENCE: 21
```

-continued gtcatcgtca tccatatggc gtctcaaggc accaaacgat c 41

<210> SEQ ID NO 22
<211> LENGTH: 39
<212> TYPE: DNA
<213> ORGANISM: Artificial Sequence
<220> FEATURE:
<223> OTHER INFORMATION: reverse primer for NP

<400> SEQUENCE: 22
gtcatcggta ccattgtcgt actcctctgc attgtctcc 39

<210> SEQ ID NO 23
<211> LENGTH: 36
<212> TYPE: DNA
<213> ORGANISM: Artificial Sequence
<220> FEATURE:
<223> OTHER INFORMATION: forward primer for MBP

<400> SEQUENCE: 23
gtcatgcata tggaagaagg taaactggta atctgg 36

<210> SEQ ID NO 24
<211> LENGTH: 33
<212> TYPE: DNA
<213> ORGANISM: Artificial Sequence
<220> FEATURE:
<223> OTHER INFORMATION: reverse primer for MBP

<400> SEQUENCE: 24
gtcatgggta cccttggtga tacgagtctg cgc 33

<210> SEQ ID NO 25
<211> LENGTH: 33
<212> TYPE: DNA
<213> ORGANISM: Artificial Sequence
<220> FEATURE:
<223> OTHER INFORMATION: forward primer for tobacco etch virus protease

<400> SEQUENCE: 25
gtcataggat ccggagaaag cttgtttaag ggg 33

<210> SEQ ID NO 26
<211> LENGTH: 40
<212> TYPE: DNA
<213> ORGANISM: Artificial Sequence
<220> FEATURE:
<223> OTHER INFORMATION: reverse primer for tobacco etch virus protease

<400> SEQUENCE: 26
gtcatcgtcg acttattaat tcatgagttg agtcgcttcc 40

<210> SEQ ID NO 27
<211> LENGTH: 23
<212> TYPE: DNA
<213> ORGANISM: Artificial Sequence
<220> FEATURE:
<223> OTHER INFORMATION: forward primer for arabinose promoter

<400> SEQUENCE: 27
ccgatcgcga aaaccaattg tcc 23

<210> SEQ ID NO 28
<211> LENGTH: 37
<212> TYPE: DNA
<213> ORGANISM: Artificial Sequence -continued
<220> FEATURE:
<223> OTHER INFORMATION: reverse primer for arabinose promoter

<400> SEQUENCE: 28
tatccccgag tacgtggtta acttcctcct gttagcc 37

<210> SEQ ID NO 29
<211> LENGTH: 24
<212> TYPE: DNA
<213> ORGANISM: Artificial Sequence
<220> FEATURE:
<223> OTHER INFORMATION: forward primer for NP gene

<400> SEQUENCE: 29
gcaagttaac atggcgtctc aagg 24

<210> SEQ ID NO 30
<211> LENGTH: 29
<212> TYPE: DNA
<213> ORGANISM: Artificial Sequence
<220> FEATURE:
<223> OTHER INFORMATION: reverse primer for NP gene

<400> SEQUENCE: 30
tttcggatcc ggtaccattg tcgtactcc 29

<210> SEQ ID NO 31
<211> LENGTH: 28
<212> TYPE: DNA
<213> ORGANISM: Artificial Sequence
<220> FEATURE:
<223> OTHER INFORMATION: forward primer for TEV protease

<400> SEQUENCE: 31
agaggagtac gacaatggta ccggatcc 28

<210> SEQ ID NO 32
<211> LENGTH: 22
<212> TYPE: DNA
<213> ORGANISM: Artificial Sequence
<220> FEATURE:
<223> OTHER INFORMATION: reverse primer for TEV protease

<400> SEQUENCE: 32
tgtccccgag ttattagcga cg 22

<210> SEQ ID NO 33
<211> LENGTH: 25
<212> TYPE: DNA
<213> ORGANISM: Artificial Sequence
<220> FEATURE:
<223> OTHER INFORMATION: forward primer for Parkin

<400> SEQUENCE: 33
acgtggatcc atgatagtgt ttgtc 25

<210> SEQ ID NO 34
<211> LENGTH: 29
<212> TYPE: DNA
<213> ORGANISM: Artificial Sequence
<220> FEATURE:
<223> OTHER INFORMATION: reverse primer for Parkin

<400> SEQUENCE: 34
tgcagtcgac ttactacacg tcgaaccag 29

-continued

<210> SEQ ID NO 35
<211> LENGTH: 30
<212> TYPE: DNA
<213> ORGANISM: Artificial Sequence
<220> FEATURE:
<223> OTHER INFORMATION: forward primer for DnaK without translational codon

<400> SEQUENCE: 35
gtcacgcata tgggtaaaat aattggtatc 30

<210> SEQ ID NO 36
<211> LENGTH: 45
<212> TYPE: DNA
<213> ORGANISM: Artificial Sequence
<220> FEATURE:
<223> OTHER INFORMATION: reverse primer for DnaK without translational codon

<400> SEQUENCE: 36
gtcacgggta cctttttgt ctttgacttc ttcaaattca gcgtc 45

<210> SEQ ID NO 37
<211> LENGTH: 42
<212> TYPE: DNA
<213> ORGANISM: Artificial Sequence
<220> FEATURE:
<223> OTHER INFORMATION: forward primer for a DnaK mutant, DnaK-V436F

<400> SEQUENCE: 37
gaagacaacc agtctgcgtt caccatccat gtgctgcagg gt 42

<210> SEQ ID NO 38
<211> LENGTH: 39
<212> TYPE: DNA
<213> ORGANISM: Artificial Sequence
<220> FEATURE:
<223> OTHER INFORMATION: reverse primer for a DnaK mutant, DnaK-V436F

<400> SEQUENCE: 38
cagcacatgg atggtgaacg cagactggtt gtcttcagc 39

<210> SEQ ID NO 39
<211> LENGTH: 36
<212> TYPE: DNA
<213> ORGANISM: Artificial Sequence
<220> FEATURE:
<223> OTHER INFORMATION: reverse primer for Do1(N-terminal domain of DnaK) without translational stop codon

<400> SEQUENCE: 39
gtcacgggta ccctaaccag tcagaacacc accctg 36

<210> SEQ ID NO 40
<211> LENGTH: 50
<212> TYPE: DNA
<213> ORGANISM: Artificial Sequence
<220> FEATURE:
<223> OTHER INFORMATION: overlapping primer 1 for the RBD1-71

<400> SEQUENCE: 40
gtcacgatta atatggcggc cgtgcaggcg gccgaggtga aagtggatgg 50

<210> SEQ ID NO 41
<211> LENGTH: 77
<212> TYPE: DNA

<213> ORGANISM: Artificial Sequence
<220> FEATURE:
<223> OTHER INFORMATION: overlapping primer 2 for the RBD1-71

<400> SEQUENCE: 41
cagcgagccg aactctgcta ctttcttctc agctttcagg cgtctcttca gctcattctt 60
gtccagtttc ggctcgc 77

<210> SEQ ID NO 42
<211> LENGTH: 65
<212> TYPE: DNA
<213> ORGANISM: Artificial Sequence
<220> FEATURE:
<223> OTHER INFORMATION: overlapping primer 3 for the RBD1-71

<400> SEQUENCE: 42
agtagcagag aaggaggcca aacagaaaga gctcagtgag aaacagctaa gccaagccac 60
tgctg 65

<210> SEQ ID NO 43
<211> LENGTH: 75
<212> TYPE: DNA
<213> ORGANISM: Artificial Sequence
<220> FEATURE:
<223> OTHER INFORMATION: overlapping primer 4 for the RBD1-71 or forward primer for RBD1-17

<400> SEQUENCE: 43
gtcacgggat cccacgctct cttcctcagg acccacacca ttatcagtgg tgtggttggt 60
ggcagcagca gtggc 75

<210> SEQ ID NO 44
<211> LENGTH: 75
<212> TYPE: DNA
<213> ORGANISM: Artificial Sequence
<220> FEATURE:
<223> OTHER INFORMATION: reverse primer for RBD1-17

<400> SEQUENCE: 44
gtcacgggat cccacgctct cttcctcagg acccacacca ttatcagtgg tgtggttggt 60
ggcagcagca gtggc 75

<210> SEQ ID NO 45
<211> LENGTH: 30
<212> TYPE: DNA
<213> ORGANISM: Artificial Sequence
<220> FEATURE:
<223> OTHER INFORMATION: forward primer for EAST6

<400> SEQUENCE: 45
atcatgacag agcagcagtg gaatttcgcg 30

<210> SEQ ID NO 46
<211> LENGTH: 33
<212> TYPE: DNA
<213> ORGANISM: Artificial Sequence
<220> FEATURE:
<223> OTHER INFORMATION: reverse primer for EAST6

<400> SEQUENCE: 46
gtcacgggat ccctatgcga acatcccagt gac 33

<210> SEQ ID NO 47

```
<211> LENGTH: 47
<212> TYPE: DNA
<213> ORGANISM: Artificial Sequence
<220> FEATURE:
<223> OTHER INFORMATION: forward primer for murine Hsc70

<400> SEQUENCE: 47

cggtcacgca tatgtctaag ggacctgcag ttggcattga tctcggc                 47


<210> SEQ ID NO 48
<211> LENGTH: 78
<212> TYPE: DNA
<213> ORGANISM: Artificial Sequence
<220> FEATURE:
<223> OTHER INFORMATION: reverse primer for murine Hsp70

<400> SEQUENCE: 48

agtgacggta ccctgaaaat acaggttttc gccgctgtca tcgtcatcgt catcatccac     60

ctcttcaatg gtggggcc                                                   78


<210> SEQ ID NO 49
<211> LENGTH: 30
<212> TYPE: DNA
<213> ORGANISM: Artificial Sequence
<220> FEATURE:
<223> OTHER INFORMATION: forward primer for AGR2(human anterior gradient
      2 homolog)

<400> SEQUENCE: 49

gtcacgggat ccatggagaa aattccagtg                                      30


<210> SEQ ID NO 50
<211> LENGTH: 27
<212> TYPE: DNA
<213> ORGANISM: Artificial Sequence
<220> FEATURE:
<223> OTHER INFORMATION: reverse primer for AGR2(human anterior gradient
      2 homolog)

<400> SEQUENCE: 50

gtcacggtcg accaattcag tcttcag                                         27


<210> SEQ ID NO 51
<211> LENGTH: 30
<212> TYPE: DNA
<213> ORGANISM: Artificial Sequence
<220> FEATURE:
<223> OTHER INFORMATION: forward primer for RPL36A(human ribosomal
      protein L36A)

<400> SEQUENCE: 51

gtcacggata tcatggttaa cgtccctaaa                                      30


<210> SEQ ID NO 52
<211> LENGTH: 30
<212> TYPE: DNA
<213> ORGANISM: Artificial Sequence
<220> FEATURE:
<223> OTHER INFORMATION: reverse primer for RPL36A(human ribosomal
      protein L36A)

<400> SEQUENCE: 52

gtcacggtcg acgaactgga tcacttggcc                                      30


<210> SEQ ID NO 53
<211> LENGTH: 60
```

```
<212> TYPE: DNA
<213> ORGANISM: Artificial Sequence
<220> FEATURE:
<223> OTHER INFORMATION: forward primer for luciferase gene

<400> SEQUENCE: 53

gtcacgggat cccaccacca ccaccacatg gaagacgcca aaaacataaa gaaaggcccg     60


<210> SEQ ID NO 54
<211> LENGTH: 33
<212> TYPE: DNA
<213> ORGANISM: Artificial Sequence
<220> FEATURE:
<223> OTHER INFORMATION: reverse primer for luciferase gene

<400> SEQUENCE: 54

gtcacgaagc ttttacacgg cgatctttcc gcc                                  33


<210> SEQ ID NO 55
<211> LENGTH: 53
<212> TYPE: DNA
<213> ORGANISM: Artificial Sequence
<220> FEATURE:
<223> OTHER INFORMATION: forward primer for lysine tRNA gene

<400> SEQUENCE: 55

gtcatcgtcg actaatacga ctcactatag ggtcgttagc tcagttggta gag            53


<210> SEQ ID NO 56
<211> LENGTH: 33
<212> TYPE: DNA
<213> ORGANISM: Artificial Sequence
<220> FEATURE:
<223> OTHER INFORMATION: reverse primer for lysine tRNA gene

<400> SEQUENCE: 56

gtcatcccat ggtggtgggt cgtgcaggat tcg                                  33


<210> SEQ ID NO 57
<211> LENGTH: 45
<212> TYPE: DNA
<213> ORGANISM: Artificial Sequence
<220> FEATURE:
<223> OTHER INFORMATION: forward primer for T7 terminator region

<400> SEQUENCE: 57

gtcatcccat ggctagcata accccttggg gcctctaaac gggtc                     45


<210> SEQ ID NO 58
<211> LENGTH: 48
<212> TYPE: DNA
<213> ORGANISM: Artificial Sequence
<220> FEATURE:
<223> OTHER INFORMATION: reverse primer for T7 terminator region

<400> SEQUENCE: 58

gtcatcgcat gccaaaaaac ccctcaagac ccgtttagag gccccaag                  48


<210> SEQ ID NO 59
<211> LENGTH: 39
<212> TYPE: DNA
<213> ORGANISM: Artificial Sequence
<220> FEATURE:
<223> OTHER INFORMATION: forward primer for a gene corresponding to a
      region ranging from 42 to 384 amino acid residues of rat
      peptidylglycine alpha-monooxygenase
```

-continued

```
<400> SEQUENCE: 59

gatatcggat cctcatttc caatgaatgc cttggtacc                          39


<210> SEQ ID NO 60
<211> LENGTH: 39
<212> TYPE: DNA
<213> ORGANISM: Artificial Sequence
<220> FEATURE:
<223> OTHER INFORMATION: reverse primer for a gene corresponding to a
      region ranging from 42 to 384 amino acid residues of rat
      peptidylglysine alpha-monooxygenase

<400> SEQUENCE: 60

atactcaagc ttctagacag gaattgggat attggcctc                          39
```

METHOD FOR IMPROVING SOLUBILITY AND FOLDING EFFICIENCY OF TARGET PROTEINS USING RNA AS MOLECULAR CHAPERONE

CROSS-REFERENCE TO RELATED APPLICATIONS

This patent application is a continuation-in-part of U.S. patent application Ser. No. 10/371,771 filed on Feb. 21, 2003 now abandoned, which claims the benefit of priority from Korean Patent Application No. 2002-0048929 filed Aug. 19, 2002, the contents of each of which are incorporated by reference herein in its entirety.

TECHNICAL FIELD

The present invention, in general, relates to a method for improving folding efficiency and solubility of a target protein, and more particularly, to a method for improving folding efficiency and solubility of a target protein linked to an RNA-binding protein by using RNA molecule as a molecular chaperone, wherein the RNA molecule interacts with the RNA-binding protein.

BACKGROUND ART

With the development of genetic recombination techniques, numerous target proteins are produced using animal cells, yeasts and prokaryotic systems including *E. coli*, and such proteins are widely used in the bioengineering industry, including medical fields. In particular, owing to its high growth rate and its relatively well identified genetic structure compared to other organisms, the bacterium *E. coli* is routinely used as a host cell for production of target proteins using genetic recombinant techniques.

However, *E. coli* has a severe disadvantage in terms of not having a variety of intracellular elements required for maturation of proteins in comparison with eukaryotic cells. In detail, post-translational modification, disulfide bond formation, glycosylation and compartmentation of proteins, which are achieved in eukaryotic cells, are not performed in *E. coli*. In addition, when a target protein is expressed in a large scale in *E. coli*, the expressed proteins frequently accumulate in the cytoplasm, forming insoluble protein aggregates referred to as inclusion bodies. Although being easily isolated and resistant to proteinase digestion, in order to obtain active proteins from the inclusion bodies, the inclusion bodies should be solubilized using a high concentration of urea or guanidium HCl to unfold proteins contained in the inclusion bodies into their primary structure, and then the resulting proteins must be refolded into biologically active conformation during or after removal of the chemical reagent. Since mechanisms associated in protein refolding are still not accurately identified, and refolding conditions vary according to proteins, finding effective refolding conditions requires much time and high cost. Because of recombinant proteins having low refolding rates, high-cost apparatuses are necessary for scaling up their industrial production, and most proteins having a high molecular weight are hard or impossible to refold, thereby creating difficulty in industrialization of such proteins.

Although biologically active proteins are stable thermodynamically, inclusion bodies are often formed during their expression in the *E. coli* system, formation of which is driven by intermolecular aggregation between folding intermediates during folding processes of proteins (Mitraki, A. and King, J., *Bio/Technology,* 7: 690-697, 1989)(Reaction Formula 1).

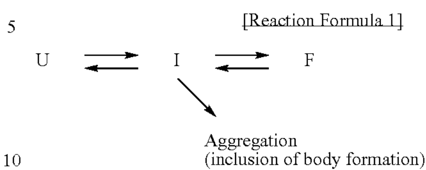

wherein, U is a protein in an unfolded state, F is a protein in a folded state, and I is a folding intermediate.

Typically, refolding a protein into an active form is accomplished experimentally, and is not always successfully achieved, thereby making large-scale production of a recombinant protein difficult. In addition, by the above-mentioned refolding process, it is difficult to obtain antibodies having a high molecular weight, tissue plasminogen activator and factor VIII in active forms.

To overcome the problems encountered when expressing target proteins as inclusion bodies, it is meaningful to express a target protein in a soluble form in *E. coli*. Until now, the following three methods have been used in effectively expressing a target protein.

First, a target protein can be obtained in a soluble form by linking a signal sequence to the N-terminus of the target protein to allow its secretion to the periplasm of *E. coli* (Stader, J. A. and Silhavy, T. *J., Methods in Enzymol.,* 165: 166-187, 1970). However, such a method is not industrially available owing to low expression rate of the target protein.

Second, a target protein can be produced in a soluble form by co-expression with a chaperone gene, such as groES, groEL or dnaK genes (Goloubinoff et al., *Nature,* 337: 44-47, 1989). The molecular chaperones assist folding of target proteins by directly shielding of hydrophobic residues of folding intermediates (Hartl, F. U. and Hayer-Hartl, M., *Science,* 295: 1852-1858, 2002).

But this method is effective for specific proteins, and so is not for general use to prevent formation of inclusion bodies.

Third, a soluble target protein can be obtained by selecting a protein highly expressed in *E. coli* and then fusing a target protein to the C-terminus of the selected protein. Such fusion of the target protein with the C-terminus of a fusion partner protein allows effective use of translation initiation signals of the fusion partner, as well as increasing solubility of the target protein linked to the fusion partner, thereby leading to large-scale expression of the target protein in a soluble form in *E. coli.*

Among the methods of the prior arts for expressing a recombinant protein in a soluble form, the most successful one is to express the recombinant protein as a fusion protein using a highly soluble protein as a fusion partner. To produce a fusion protein in *E. coli*, Lac Z or Trp E protein is conventionally used as a fusion partner protein. However, fusion proteins with the Lac Z or Trp E protein are mostly produced as inclusion bodies, and thus it is hard to obtain a protein of interest in an active form. In this regard, many attempts to find new fusion partner proteins have been performed. As a result, several proteins or peptides were developed as fusion partner proteins: glutathion-5-transferase (Smith, D. B. and Johnson, K. S., *Gene,* 67: 31-40, 1988), maltose-binding protein (Bedouelle, H. and Duplay, P., *Euro. J. Biochem.,* 171: 541-549, 1988), protein A (Nilsson et al., *Nucleic Acid Res.,* 13: 1151-1162, 1985), Z domain of protein A (Nilsson et al., *Prot. Eng.,*

1: 107-113, 1987), protein Z (Nygren et al., *J. Mol. Recog.,* 1: 69-74, 1988), and thioredoxin (Lavallie et al., *Bio/Technology,* 11: 187-193, 1993).

It has been reported that factors determining solubility of proteins include, in order of importance, average charge, fraction of turn-forming residues, cysteine fraction, proline fraction, hydrophilicity and total numbers of residues. And it also has been reported that average net charge and fractions of turn-forming residues are especially important (Wilkinson, D. L. and Harrison, R. G., *Bio/Technology,* 9: 443-448, 1991). Using the two very important parameters, model formula for solubility of a protein is defined as follows (Davis et al., *Biotechnol. Bioeng.,* 65: 382-388, 1999):

<Model Foumula>

$$CV=\lambda 1((N+G+P+S)/n)+\lambda 2|((R+K)-(D+E))/n-0.03)|$$

wherein, CV is a canonical variable; n is the number of amino acids in the protein; N, G, P and S are numbers of residues of asparagine (N), glycine (G), proline (P) and serine (S), respectively; R, K, D and E are numbers of residues of arginine (R), lysine (K), asparaginic acid (D), glutamic acid (E), respectively; and λ1 and λ2 are coefficients of 15.43 and −29.56, respectively. If CV−CV' is positive, a protein is predicted to be insoluble. If CV−CV' is negative, a protein is predicted to soluble.

In the above formula, probability of solubility or insolubility is designated as 0.4934+0.276βCV−CV'|−0.0392(CV−CV')2, where CV' is a discriminant number of 1.71. That is, solubility of protein is determined by average charge and folding rate, where the higher the content of turn-forming residues including Asn, Gly, Pro and Ser is, the lower the folding rate is. Using the above formula, the *E. coli* protein Nus A was developed as a fusion partner (Davis et al., *Biotechnol. Bioeng.,* 65: 382-388, 1999).

As described above, among the methods of the prior arts for expressing a recombinant protein as a soluble form, the most successful one is to express the recombinant protein as a fusion protein using a protein having high solubility as a fusion partner. The conventional fusion partner proteins include maltose binding protein, thioredoxin, glutathione-5-transferase, NusA, LysN (N-terminal domain of *E. coli* lysine tRNA synthetase), and lysS (Korean Pat. NO: 203919). A fusion partner protein improves solubility of a target protein according to Reaction Formula 2, below.

[Reaction Formula 2]

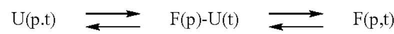

wherein, U is an unfolded state; F is a folded state; p is a fusion partner; and t is a target protein.

As apparent in the above Reaction Formula 1, the fusion protein increases overall solubility of the target protein by stabilizing intermediates using its high soluble property.

Molecular chaperones are protein molecules known to help folding of proteins by temporarily binding to partially folded proteins and thus preventing their aggregation. Referring to the above Reaction Formula 2, a fusion partner is considered to serve as a chaperone. Because of being linked to a target protein, the fusion partner can be referred to a molecular chaperone. In the conventional concept of the molecular chaperones, a prosequence of a protein, for example, that of subtilisin, which is cleaved after assisting folding of a protein, is called a molecular chaperone (Shinde, U. and Inouye, M., *J. Mol. Biol.* 247(3): 390-395, 1995). There is a difference between the prosequence and the fusion partner. The former has a limitation of acting to assist folding of only one protein, while the latter helps folding of a broad range of target proteins. Also, it has been reported that ribosome or the ribosomal component 23S RNA help refolding of proteins (Das et al., *Eur. J. Biochem.,* 235: 623-621, 1996; Chattopadhyay et al., *Proc. Natl. Acad. Sci. U.S.A.,* 93: 8284-8287, 1996). The utility of the process is very limited, however. The in vitro refolding process still requires chemical agents such as urea or guanidium HCl for unfolding of target proteins. The chemical reagents must be diluted and removed after the refolding process, which is time-consuming and laborious. Moreover, the 23 rRNA does not provide efficient interaction with most proteins and therefore the repertoire of proteins that would be folded by this process is extremely limited.

The ability of the fusion partner proteins to exert folding of the fused target proteins may basically depend on a rapid folding rate and high average net charge. The most urgent prior problem to be solved in the post-genome era is to identify the function of proteins. To solve the above problem, proteins are first produced in a soluble active form. In this regard, development of fusion partner proteins having excellent properties is very important in basic research and industrial processes. Fusion partner proteins have been discovered by experimental experiences or an aforementioned simple method, like the discovery of NusA.

SUMMARY OF THE INVENTION

The present invention provides a method for improving folding efficiency and solubility of a target protein linked to a RNA-binding protein by using RNA molecule as a molecular chaperone, wherein the RNA molecule interacts with the RNA-binding protein.

In an embodiment of the present invention, the RNA molecule is selected from the group consisting of mRNA, tRNA, rRNA, nuclear RNA, non-coding RNA, viral RNA and ribopolynucleotides prepared by genetic recombination techniques.

In a preferred embodiment of the present invention, the RNA-binding protein is selected from the group consisting of tRNA-binding proteins, ribosomal proteins, mRNA-binding proteins, non-coding RNA binding protein, viral proteins having RNA-binding ability and proteins associated with cellular RNA processing and turnover, or a polypeptide corresponding to an RNA-binding domain of the aforementioned proteins.

In a more preferred embodiment, the RNA-binding protein is selected from the group consisting of *E. coli* Lysyl-tRNA synthatase, C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain of the aforementioned proteins.

In another preferred embodiment, the RNA molecule is naturally present in cells and interacts with the RNA-binding protein.

In a more preferred embodiment, the RNA molecule is artificially over-expressed by constructing a vector expressing said RNA molecule and then introducing the vector into a host cell.

In another preferred embodiment, the method comprises the steps of:

1) constructing an expression vector encoding a fusion protein in which the target protein is linked to an RNA-binding protein;

2) constructing an expression vector expressing an RNA molecule capable of binding to the RNA-binding protein linked to the target protein; and 3) cotransforming a host cell with the expression vectors prepared in steps 1 and 2.

In a more preferred embodiment, the host cell is *E. coli, B. subtilis, S. serevisiae, S. pombe, H. polymorpha, P. pastoris*, an insect cell, a plant cell or a mammalian cell.

The present invention also provides a method for producing a target protein having improved solubility and folding efficiency using an RNA molecule as a molecular chaperone, comprising expressing the target protein linked to an RNA-binding protein, and forming a ribonucleoprotein (RNP) complex between an RNA molecule and the RNA-binding protein.

In an embodiment, the RNA molecule is selected from the group consisting of mRNA, tRNA, rRNA, nuclear RNA, non-coding RNA, viral RNA and ribo-polynucleotides prepared by genetic recombination techniques.

In a more preferred embodiment, the RNA-binding protein is selected from the group consisting of tRNA binding proteins, ribosomal proteins, mRNA-binding proteins, non-coding RNA-binding protein, viral proteins having RNA-binding ability and proteins associated with cellular RNA processing and turnover, or a polypeptide corresponding to an RNA-binding domain of the aforementioned proteins.

In another preferred embodiment, the RNA-binding protein is selected from the group consisting of *E. coli* Lysyl-tRNA synthatase, C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain of the aforementioned proteins.

In a more preferred embodiment, the RNA molecule is naturally present in cells and interacts with the RNA-binding protein.

In another preferred embodiment, the RNA molecule is artificially over-expressed by constructing a vector expressing said RNA molecule and then introducing the vector into a host cell.

In a more preferred embodiment, the method comprises the steps of:

1) constructing an expression vector encoding a target protein linked to an RNA-binding protein;

2) constructing an expression vector expressing an RNA molecule capable of binding to the RNA-binding protein linked to the target protein; and 3) cotransforming a host cell with the expression vectors prepared in steps 1 and 2.

Further, the present invention provides a method for producing a target protein having improved solubility and folding efficiency in intact form comprises the steps of:

1) constructing a first gene cassette comprising a polynucleotide encoding an RNA-binding protein, a polynucleotide encoding a recognition sequence for a sequence-specific protease and a gene encoding the target protein;

2) constructing a second gene cassette comprising a polynucleotide encoding the sequence-specific protease;

3) co-transforming a host cell with the first gene cassette and the second gene cassette;

4) culturing the co-transformed host cell in an appropriate culture medium; and 5) recovering the target protein from the culture media or cell lysate.

In an embodiment, the RNA-binding protein is selected from the group consisting of tRNA-binding proteins, ribosomal proteins, mRNA binding proteins, non-coding RNA binding proteins, viral proteins having RNA-binding ability and proteins associated with cellular RNA processing and turnover, or a polypeptide corresponding to an RNA-binding domain of the aforementioned proteins.

In a more preferred embodiment, the RNA-binding protein is selected from the group consisting of C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain of the aforementioned proteins.

In a preferred embodiment, the sequence-specific protease is enterokinase, factor Xa or TEV protease In a preferred embodiment, the first gene cassette and/or the second gene cassette further comprise promoter.

BRIEF DESCRIPTION OF THE DRAWINGS

The above and other objects, features and other advantages of the present invention will be more clearly understood from the following detailed description taken in conjunction with the accompanying drawings, in which.

M: molecular marker;

T: whole cell lysate;

S: supernatant; and

P: pellet.

FIG. 4*a* is a photograph showing results of comparing solubility of LysN-TEV and LysRS-TEV, and FIG. 4*b* is a photograph showing results of comparing solubility of other target proteins fuses with LysN and LysRS:

M: molecular marker;

T: whole cell lysate;

S: supernatant; and

P: pellet.

Figure 5:
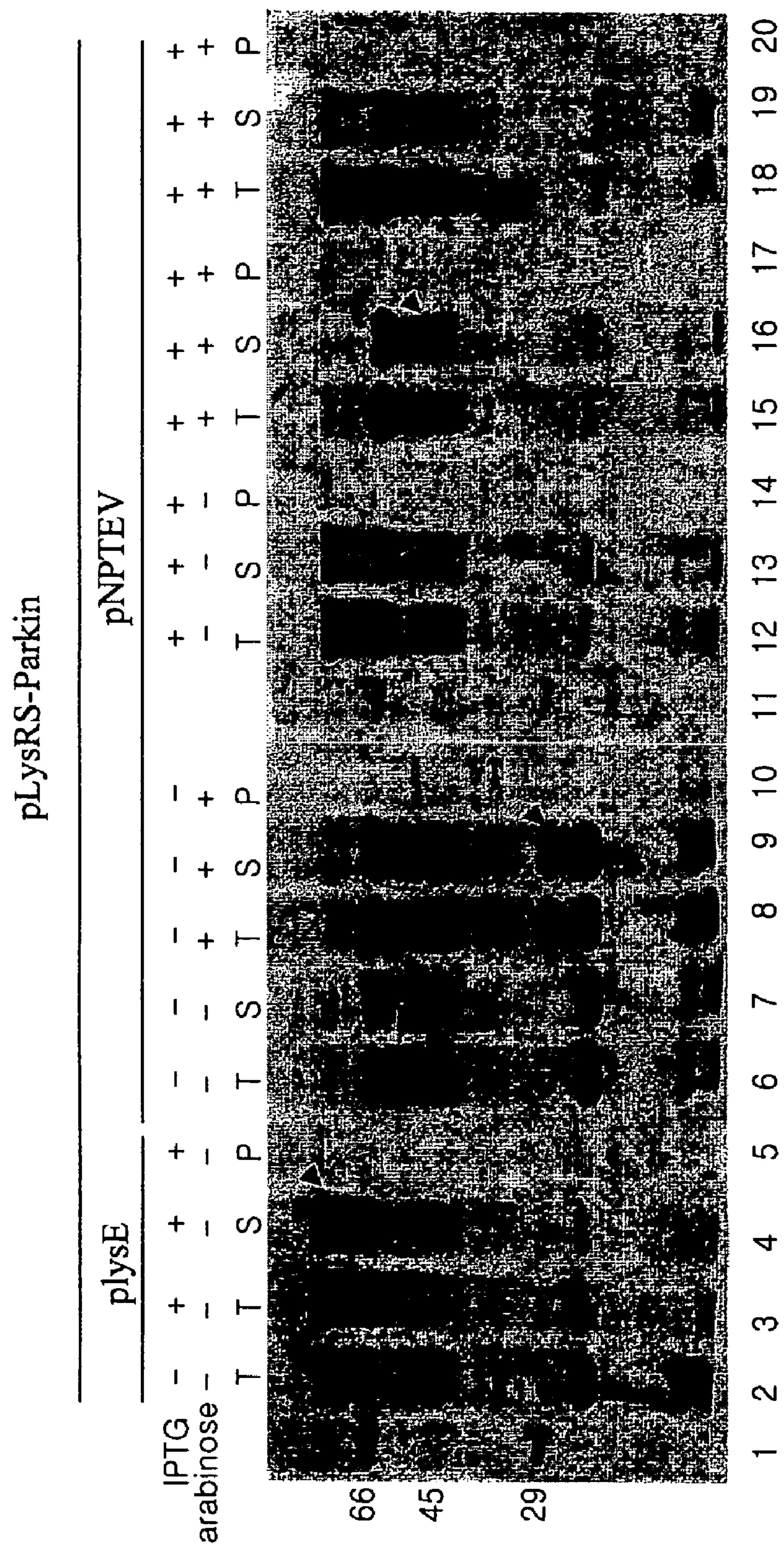

FIG. 5 is a photograph showing controlled intracellular processing (CIP) of fusion proteins with NP-TEV protease.

M: molecular marker;

T: whole cell lysate;

S: supernatant;

P: pellet; and

Arrow: expressed target proteins.

Figure 6:
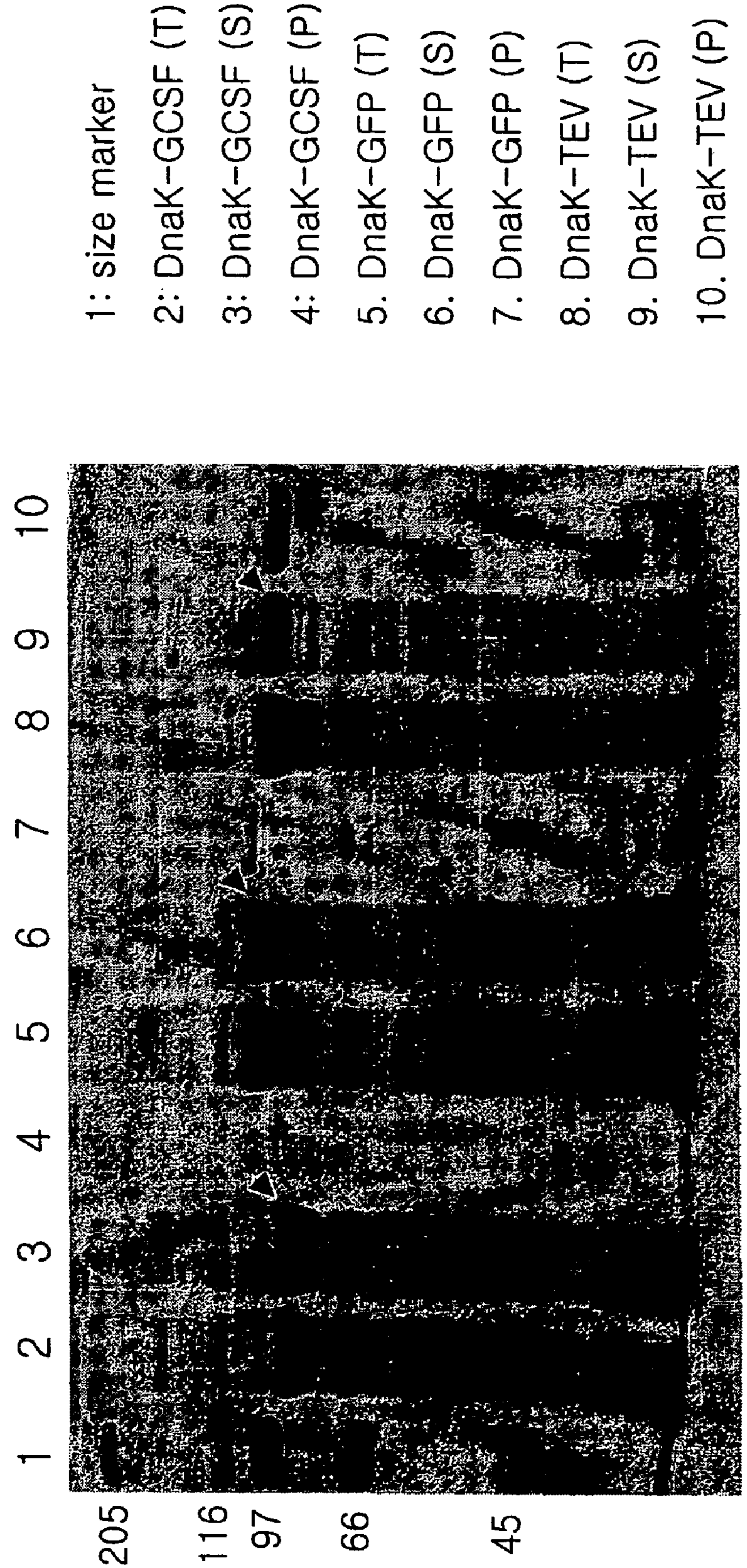

FIG. 6 is a photograph showing results of SDS-PAGE when DnaK is used as a fusion partner with various target proteins such as GCSF, GFP and TEV:

Arrow: expressed target proteins.

Figure 7:
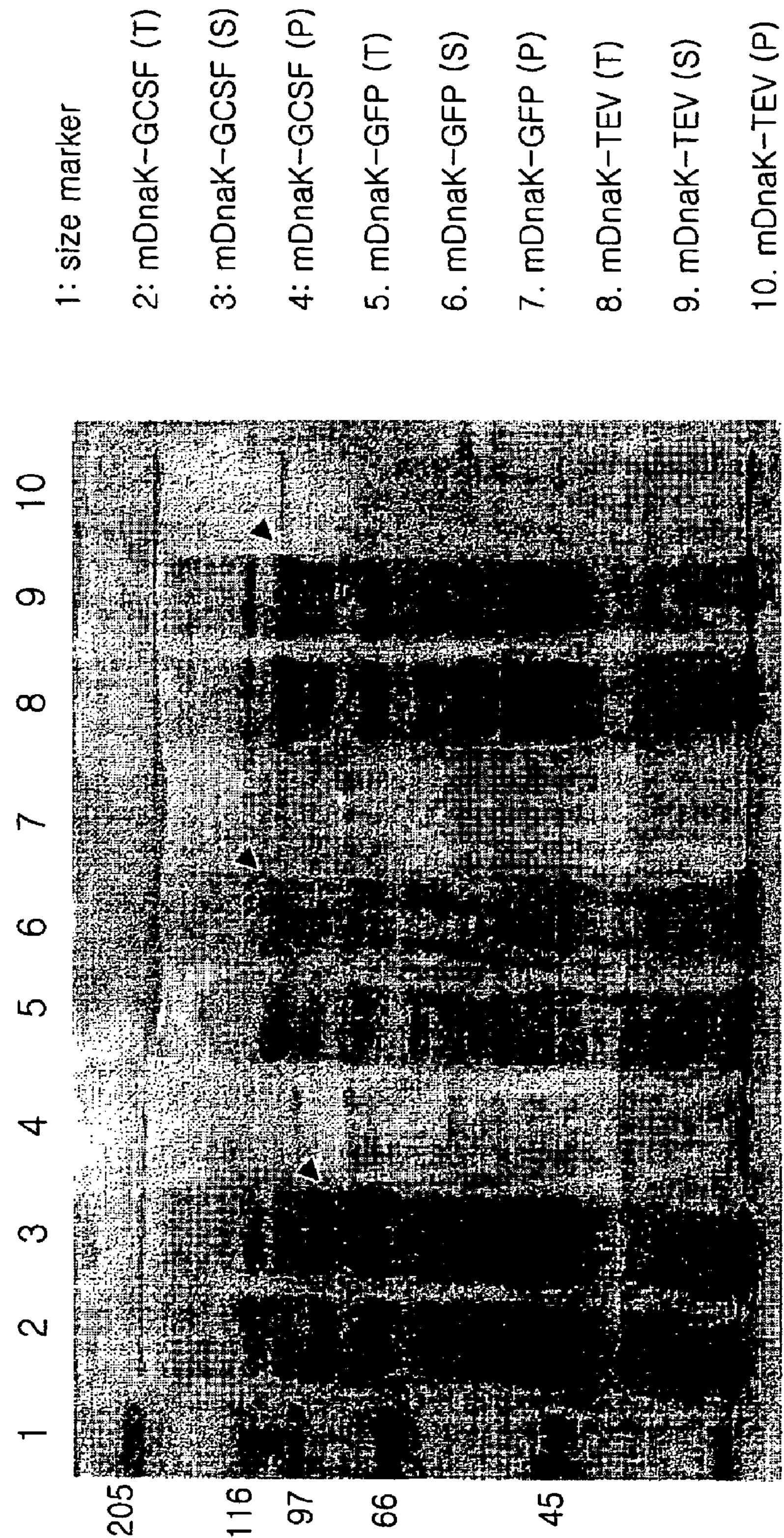

FIG. 7 is a photograph showing results of SDS-PAGE when a DnaK mutant, DnaK-V436F is used as a fusion partner with various target proteins such as GCSF, GFP and TEV:

Arrow: expressed target proteins.

Figure 8:
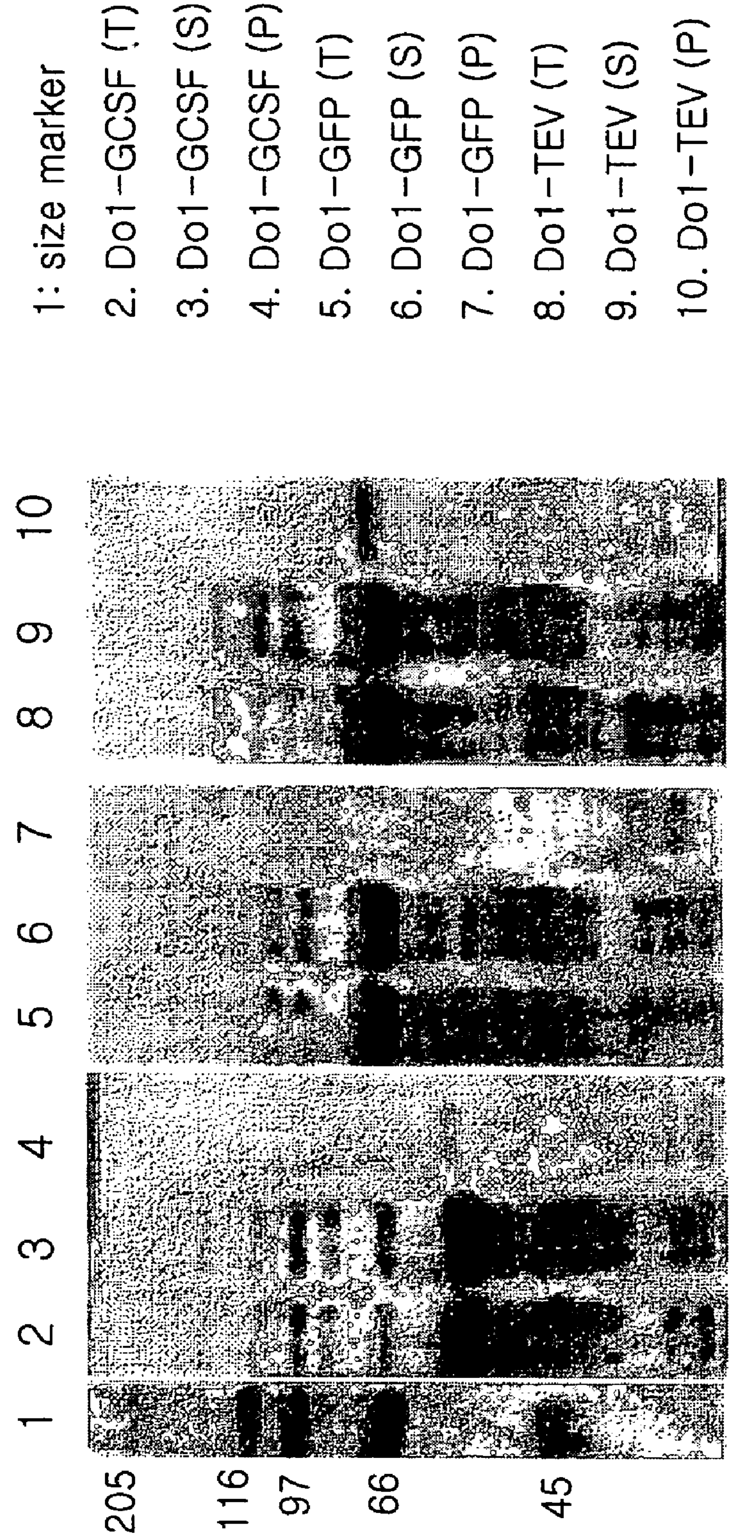

FIG. 8 is a photograph showing results of SDS-PAGE when an N-terminal of DnaK (Do1) is used as a fusion partner with various target proteins such as GCSF, GFP and TEV.

Figure 9:
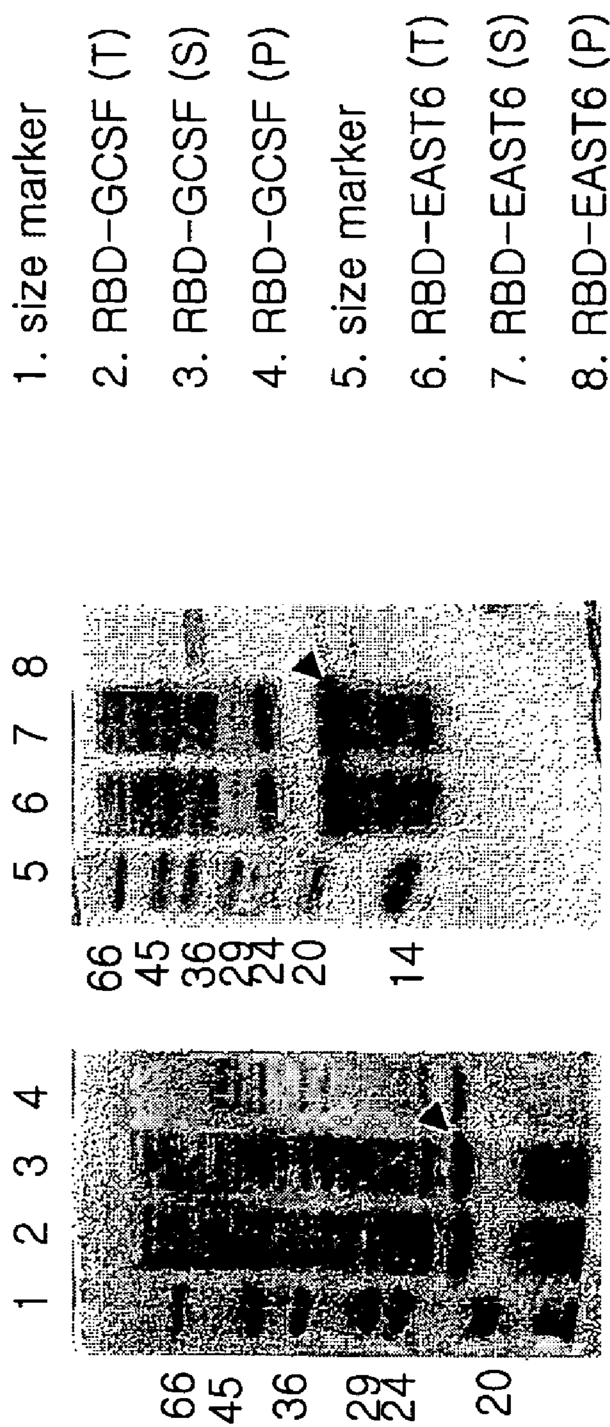

FIG. 9 is a photograph showing results of SDS-PAGE when an N-terminal domain of human lysyl-tRNA synthetase ($hLRS_{1-17}$) is used as a fusion partner with various target proteins such as GCSF and EAST6:

Arrow: expressed target proteins.

Figure 10:
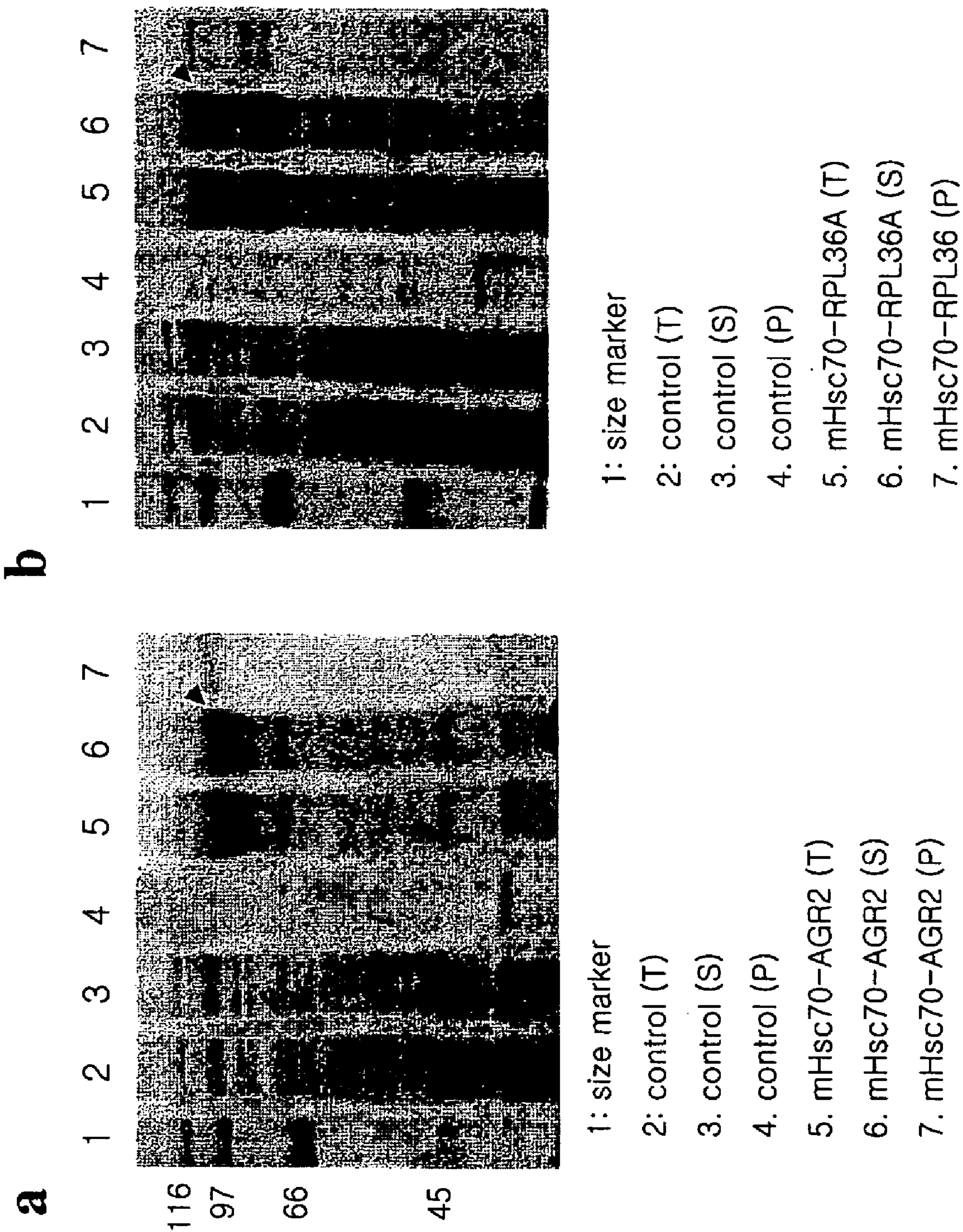

FIG. 10 is a photograph showing results of SDS-PAGE when murine Hsc70 is used as a fusion partner with various target proteins such as AGR2 (a) and RPL36A (b):

Arrow: expressed target proteins.

Figure 11:
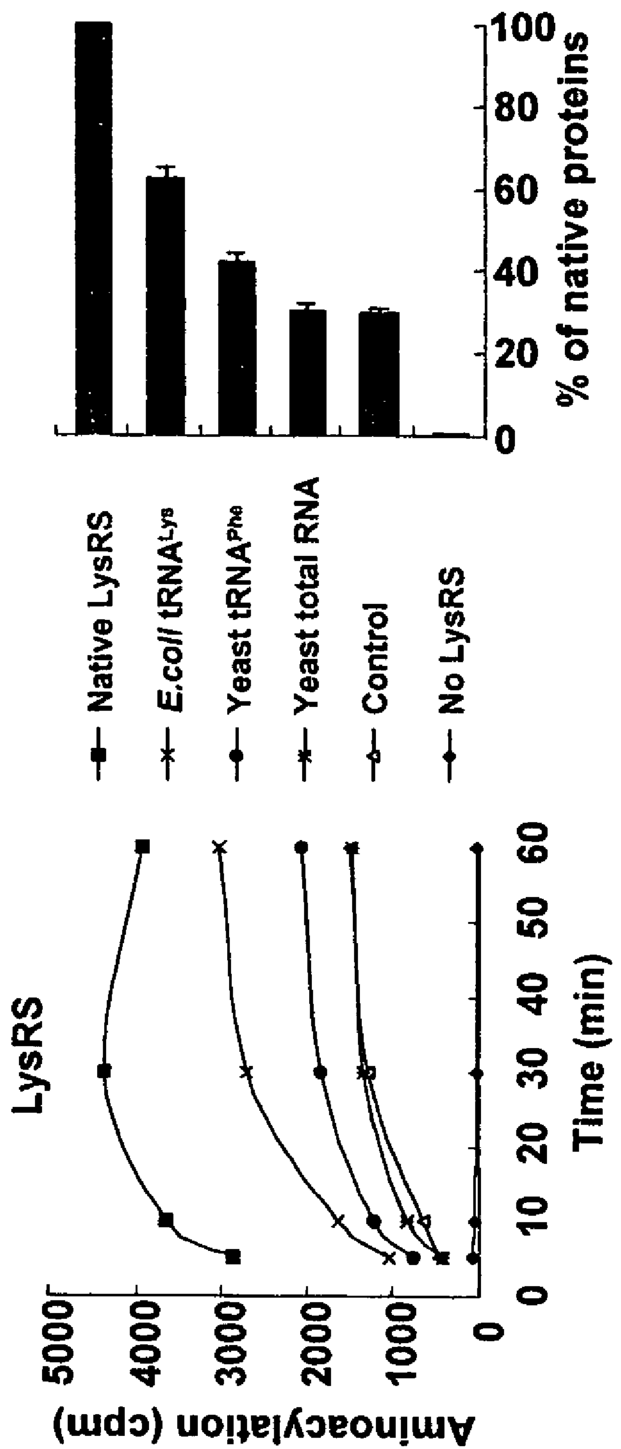

FIG. 11 is a graph showing folding efficiency of LysRS in vitro.

Figure 12:
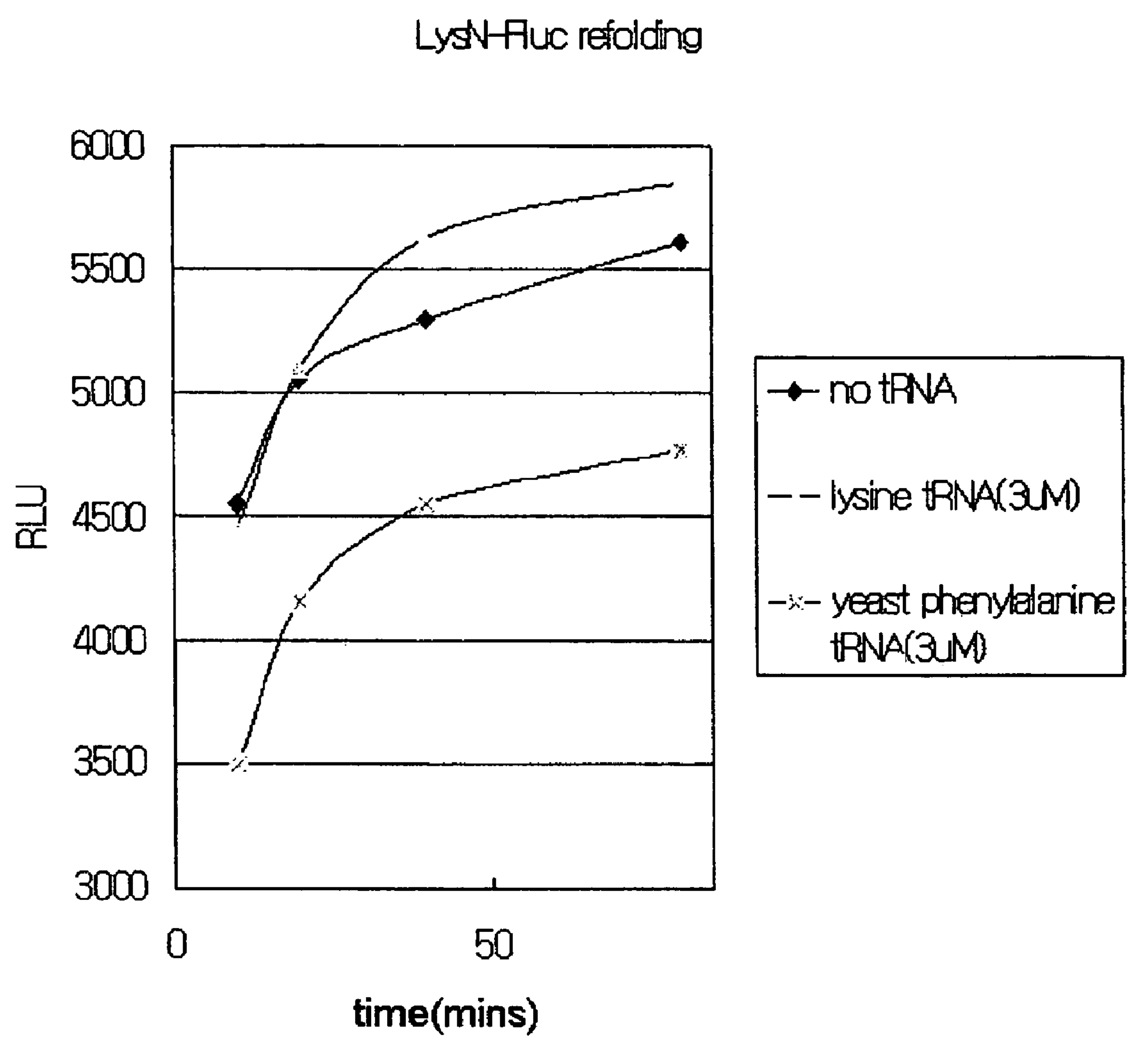

FIG. 12 is a graph showing result of luciferase activity analysis for determining the effect of lysine tRNA on refolding of a LysRs-firefly luciferase fusion protein.

Figure 13:
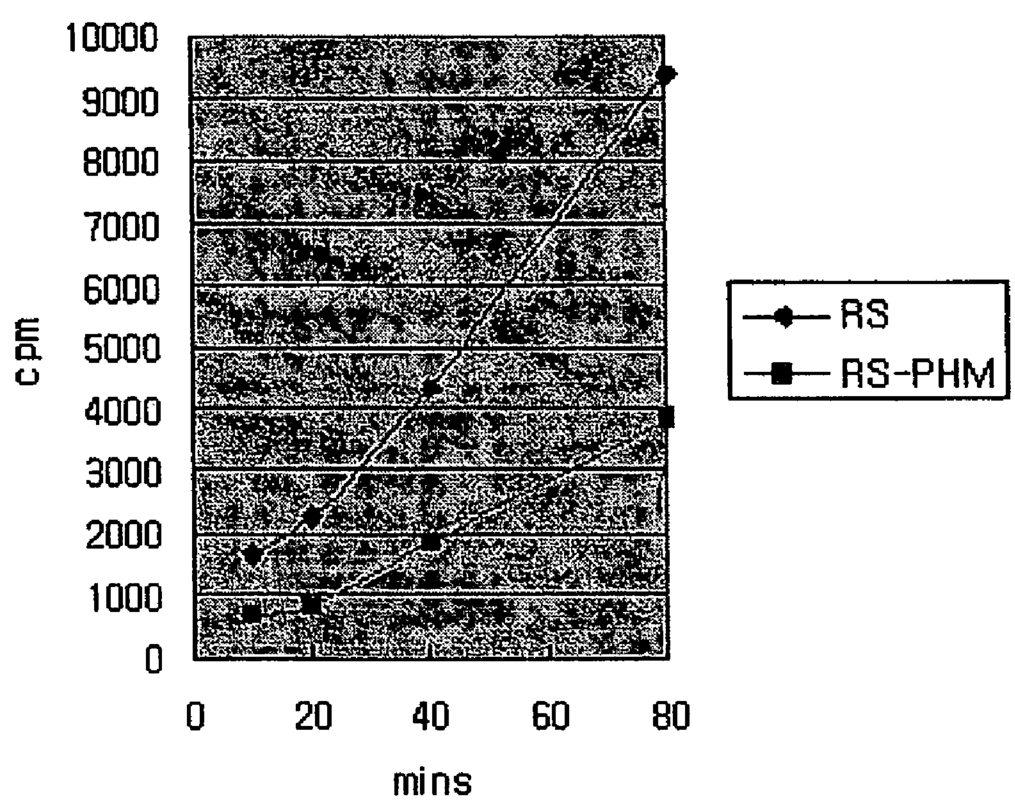

FIG. 13*a* is a photograph showing results of SDS-PAGE of isolated LysRS and LysRS-PHM proteins, and FIG. 13*b* is a graph showing results of tRNA synthetase activity analysis for the LysRS and LysRS-PHM proteins to identify binding of the LysRS-PHM protein to lysine tRNA.

Figure 14:
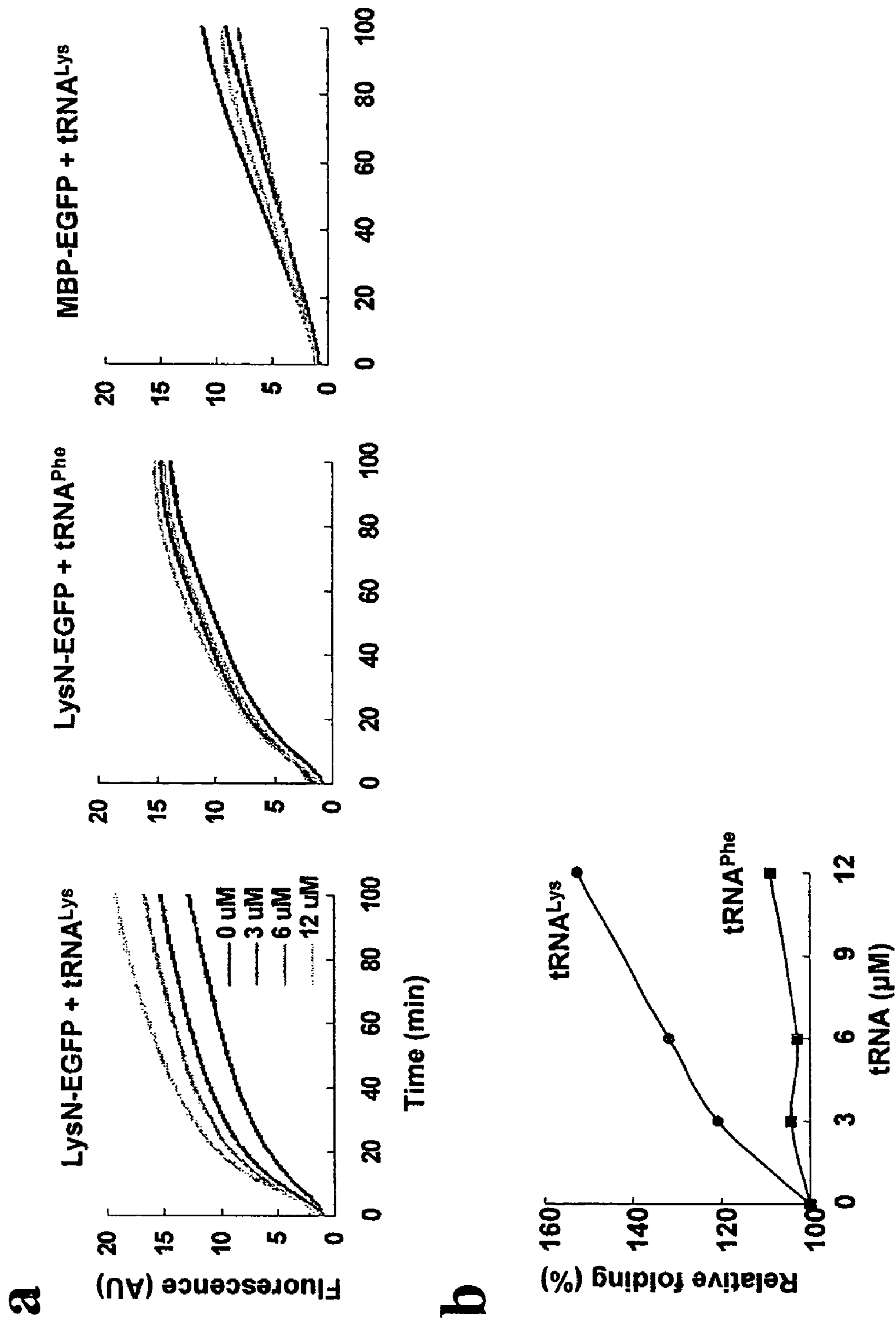

FIG. 14*a* is a series of graphs showing results of refolding efficiency of Lys-EGFP with $tRNA^{Lys}$ and $tRNA^{Phe}$ and FIG. 14*b* is a graph showing difference of folding efficiency according to binding specificity between tRNA and tRNA synthetase.

Figure 15:
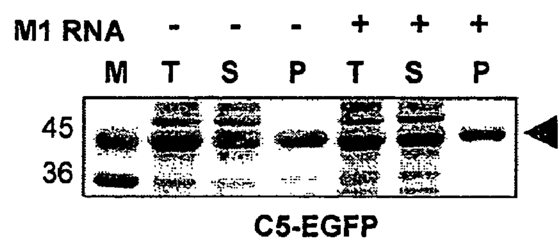
Figure 15:
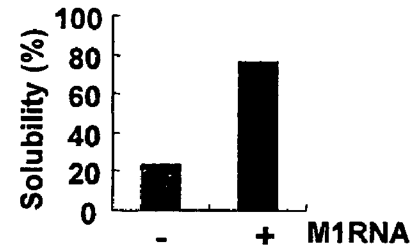
Figure 15:
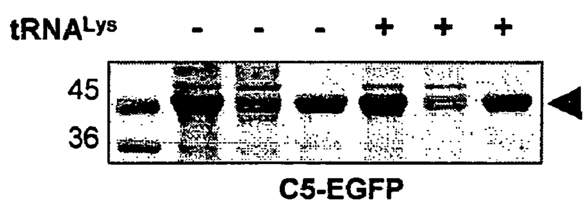
Figure 15:
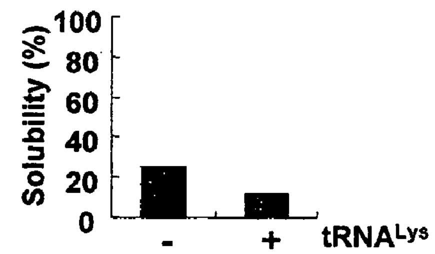

FIG. 15*a* is a photograph showing results of RNA-mediated protein folding in vivo when C5 protein is used as an RNA-binding protein and EGFP is a reporter protein with or without M1 RNA and FIG. 15*b* is a photograph showing results of RNA-mediated protein folding in vivo when C5 protein is used as an RNA-binding protein and EGFP is a reporter protein with or without $tRNA^{Lys}$:

Arrowhead: expressed target proteins.

Figure 16:
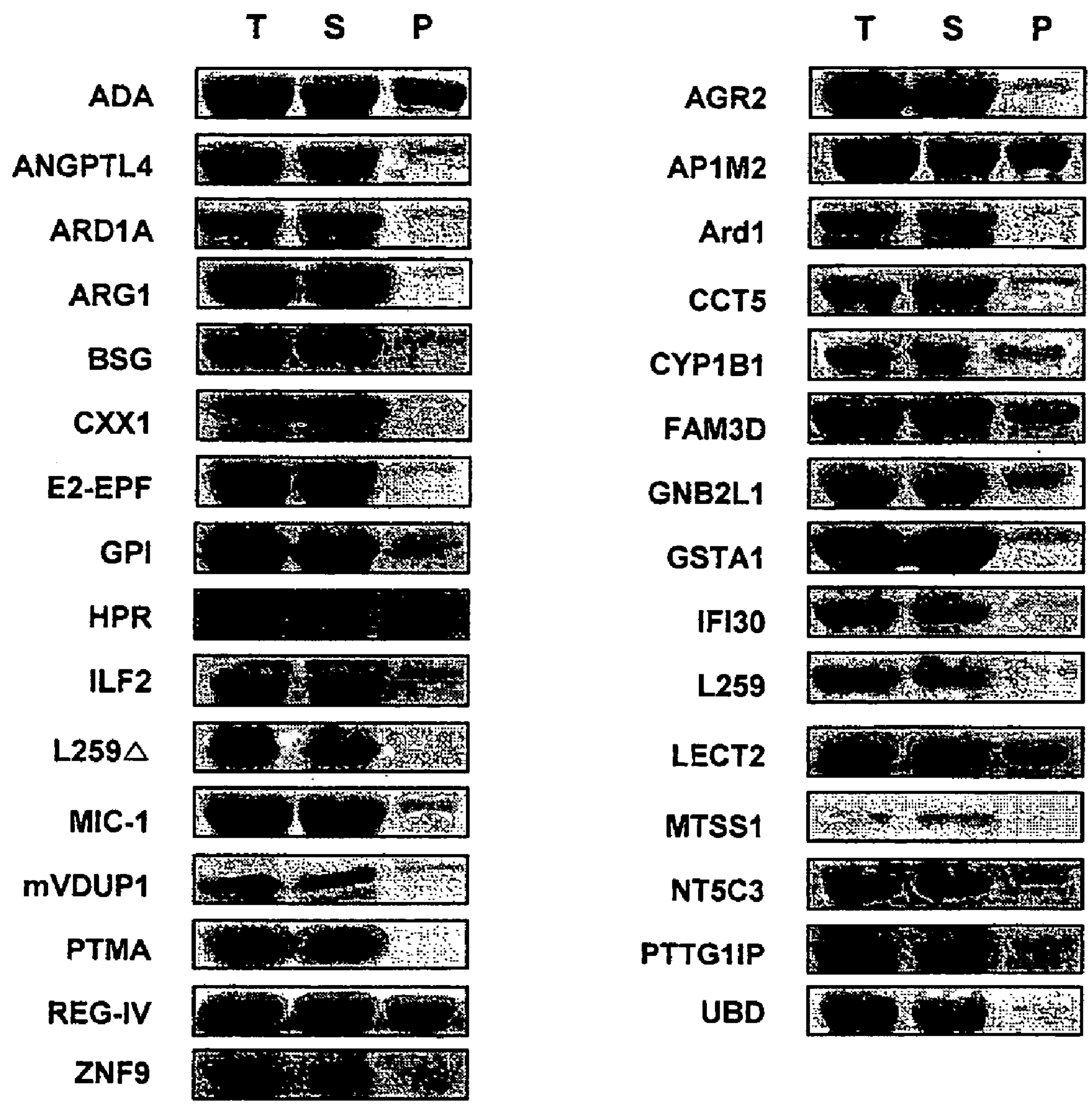

FIG. 16 is a photograph showing results of SDS-PAGE performed with various target proteins using the expression system of the present invention:

T: whole cell lysate;

S: supernatant; and

P: pellet.

Figure 17:
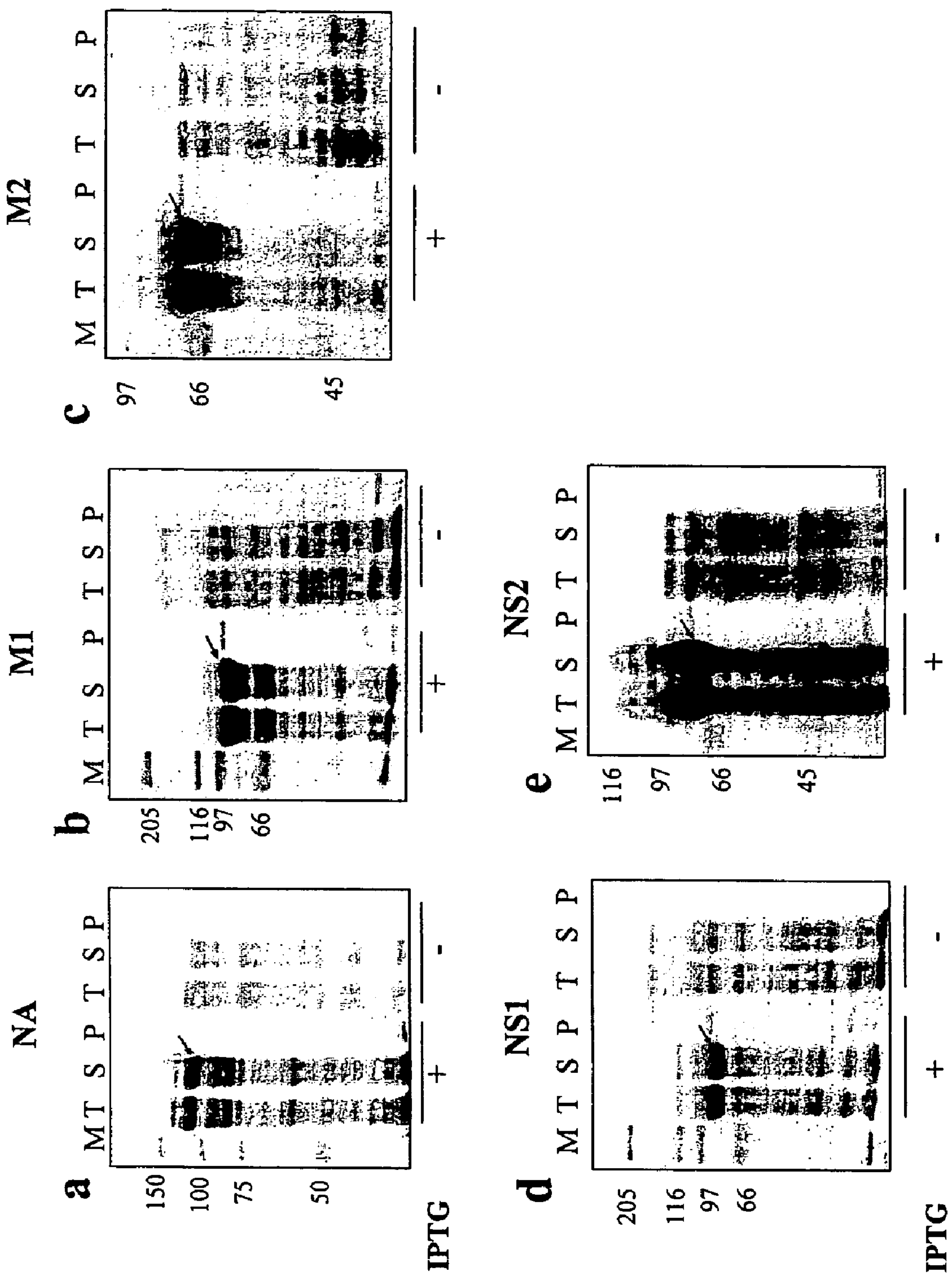

FIG. 17 is a series of photograph showing results of SDS-PAGE performed with various proteins of influenza virus A such as NA (a), M1 (b), M2(c) NS1 (d) and NS2 (e) using the expression system of the present invention:

M: molecular marker;

T: whole cell lysate;

S: supernatant;

P: pellet; and

Arrow: expressed target proteins.

Figure 18:
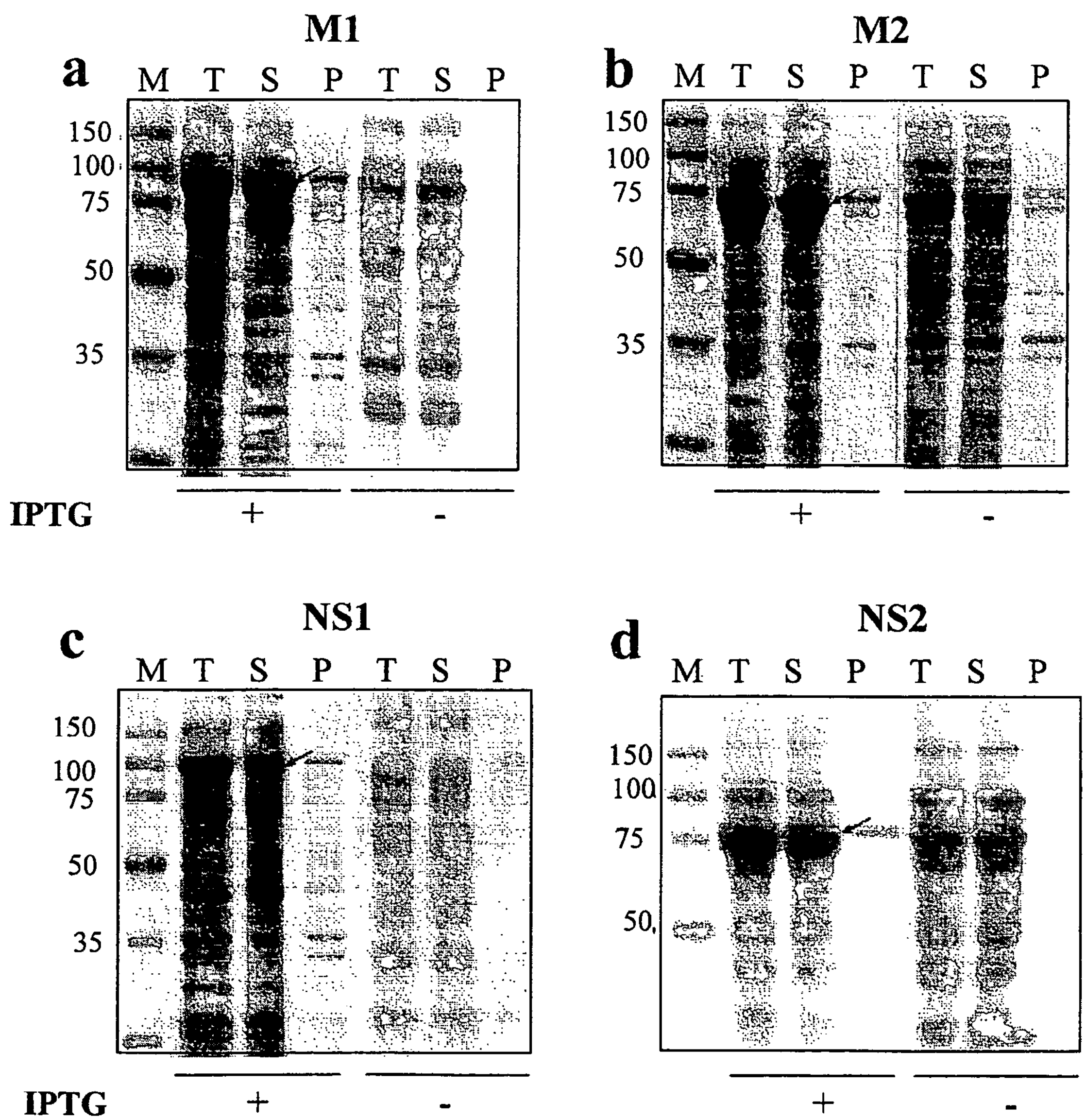

FIG. 18 is a series of photograph showing results of SDS-PAGE performed with various proteins of influenza virus B such as M1 (a), M2 (b), NS1 (c) and NS2 (d) using the expression system of the present invention:

M: molecular marker;

T: whole cell lysate;

S: supernatant;

P: pellet; and

Arrow: expressed target proteins.

Figure 19:
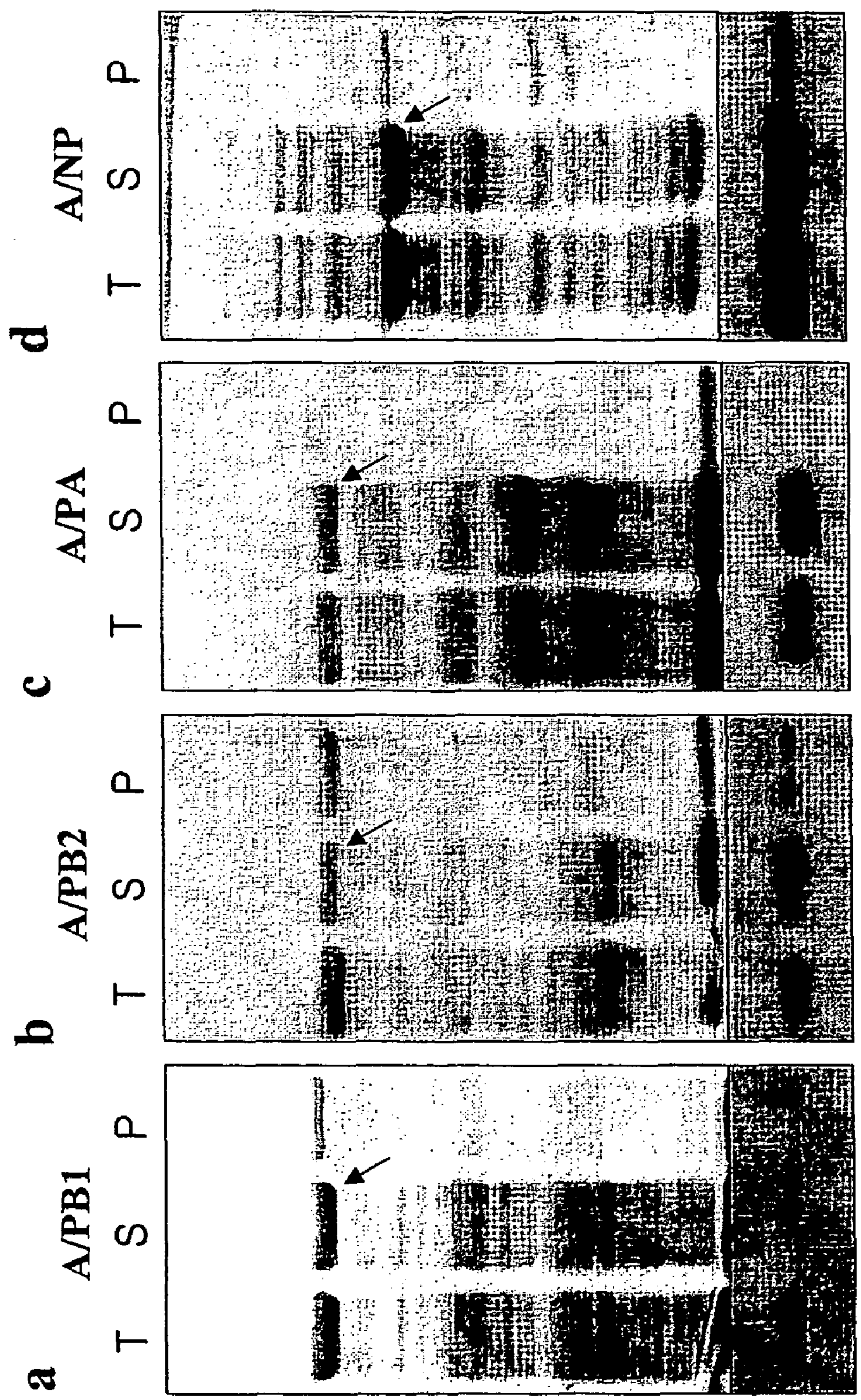

FIG. 19 is a series of photographs showing results of SDS-PAGE performed with various proteins of influenza RNA polymerase of influenza strain A/WSN/33 including PB1 (a), PB2 (b), PA (c) and NP (d) using the expression system of the present invention:

T: whole cell lysate;

S: supernatant;

P: pellet; and

Arrow: expressed target proteins.

Figure 20:
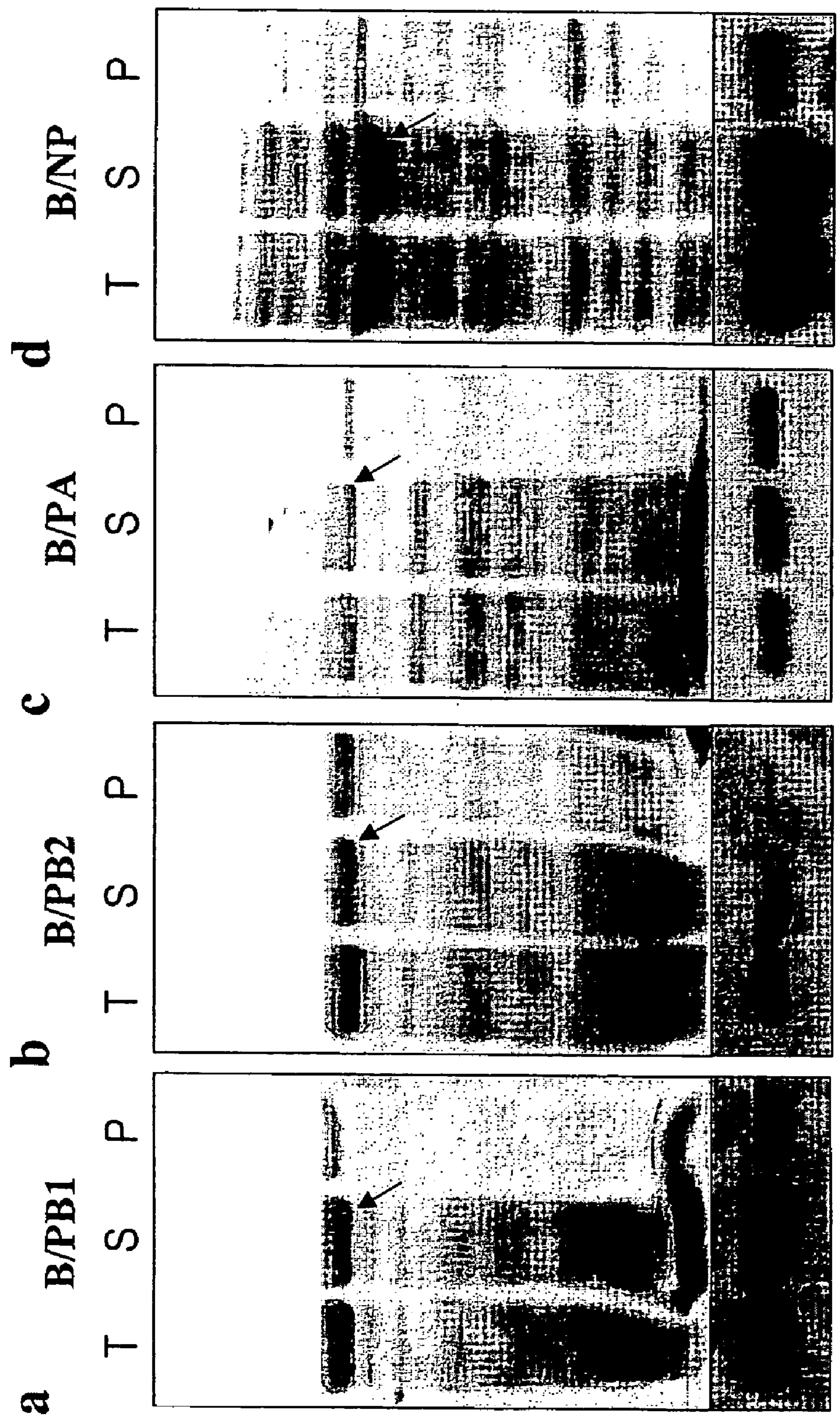

FIG. 20 is a series of photographs showing results of SDS-PAGE performed with various proteins of influenza RNA polymerase of influenza strain B/Lee/40 including PB1 (a), PB2 (b), PA (c) and NP (d) using the expression system of the present invention:

T: whole cell lysate;

S: supernatant;

P: pellet; and

Arrow: expressed target proteins.

Figure 21:
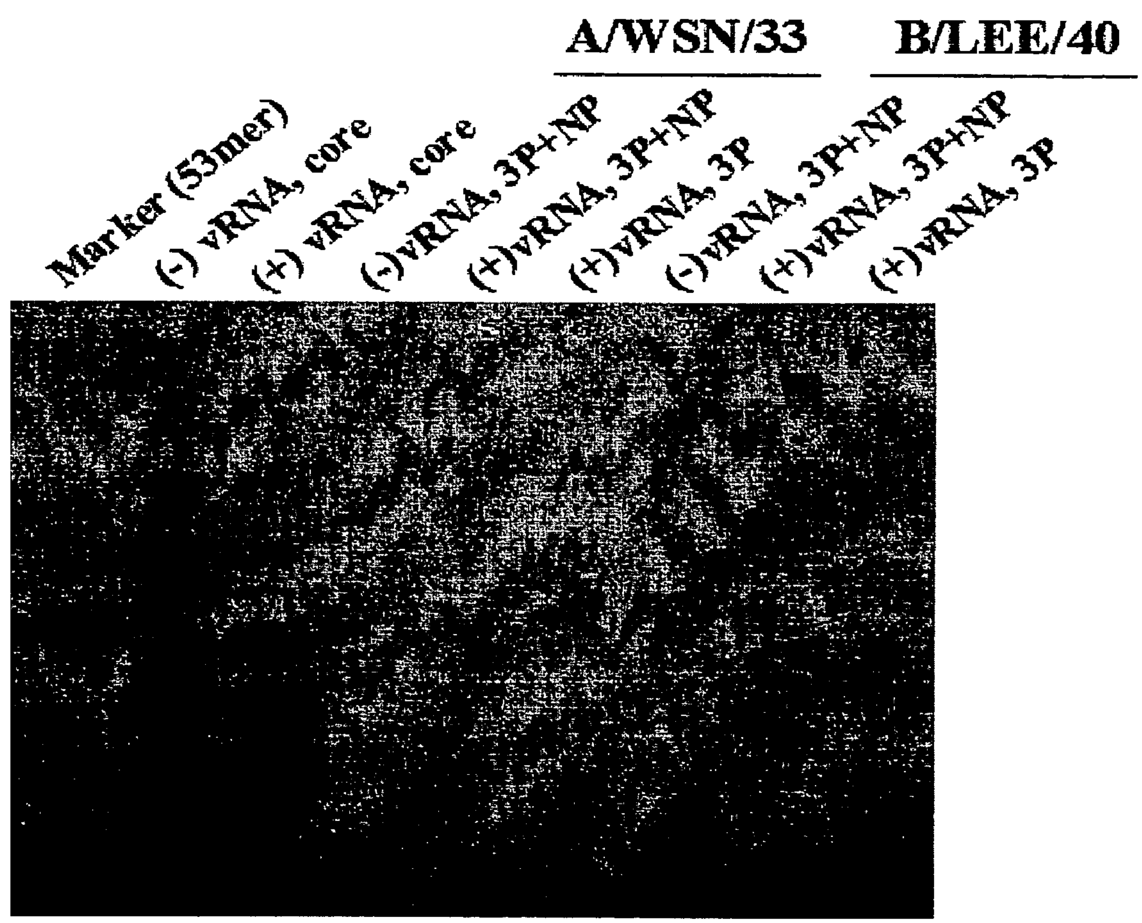

FIG. 21 is a photograph showing results of successful reconstitution of RNA polymerase using the expression system of the present invention.

Figure 22:
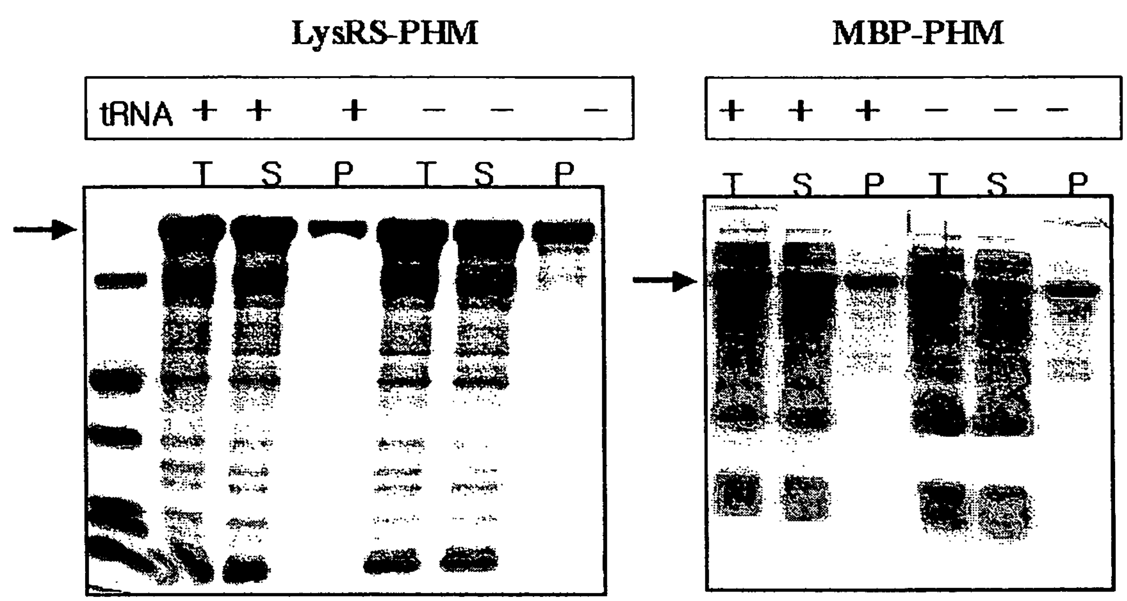

FIG. 22 is a photograph showing results of SDS-PAGE analysis for solubility of fusion proteins obtained by expressing a target protein as a fusion protein at 37° C. or 27° C. using various RNA-binding proteins to construct the fusion proteins:

M: molecular marker;

T: whole cell lysate;

S: supernatant;

P: pellet; and

Arrow: expressed target proteins.

BEST MODES FOR CARRYING OUT THE INVENTION

1. Definitions

Unless otherwise indicated, all technical and scientific terms used herein have the same meaning as they would to one skilled in the art of the present invention. Practitioners are particularly directed to Sambrook et al., 1989, and Ausubel F. M. et al., 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "polynucleotide" includes RNA, DNA and cDNA molecules.

The term "folding efficiency" as used herein refers to an extent how many protein molecules form their intricate three-dimensional shape.

The term "RNA-binding protein" as used herein refers to a protein which binds RNA molecule specifically or nonspecifically. It includes RNA-binding domain thereof.

The term "domain" or "protein domain" as used herein refers an independently folded structural unit of a protein.

The term "fusion protein" as used herein refers a protein consisting of two or more distinctive proteins or domains.

The term "target protein" as used herein refers a protein to be expressed

As used herein, the terms "transformed" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, filamentous fungi, plant, insect, amphibian, or mammalian cells.

As used herein, the term "vector" refers to a nucleic acid construct designed for transfer between different host cells.

An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, a "gene cassette" or "gene construct" is a nucleic acid construct generated recombinantly or synthetically, with a series of specified nucleic acid elements that permit transcription of a particular nucleic acid in a target cell. The gene cassette can be incorporated into a plasmid, chromosome, mitochondrial DNA, plastid DNA, virus, or nucleic acid fragment. Typically, the gene expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extra-chromosomal self-replicating genetic element in many bacteria and some eukaryotes.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, the term "target protein" means a protein or peptide to be expressed recombinantly.

2. Detailed Description of the Invention

To achieve the aforementioned object, the present invention provides a method for improving folding efficiency and solubility of a target protein linked to a RNA-binding protein by using RNA molecule as a molecular chaperone, wherein the RNA molecule interacts with the RNA-binding protein.

The RNA-binding protein is selected from a group consisting of tRNA binding proteins, ribosomal RNA binding proteins, mRNA-binding proteins, non-coding RNA binding proteins, viral proteins having RNA-binding ability and proteins associated with cellular RNA-processing and turn over, or a polypeptide corresponding to an RNA-binding domain of the aforementioned proteins, but not limited thereto.

In a more preferable embodiment, the RNA-binding protein is selected from the group consisting of *E. coli* Lysyl-tRNA synthatase, C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain (RBD) of the aforementioned proteins.

In a preferred embodiment, the RNA molecule is selected from the group consisting of mRNA, tRNA, rRNA, nuclear RNA, non-coding RNA, viral RNA and ribo-polynucleotides prepared by genetic recombination techniques, but not limited thereto.

In another preferred embodiment, the RNA molecule is an RNA molecule naturally present in cells, or an artificially co-expressed RNA molecule, but not limited thereto.

In an embodiment, the host cell is *E. coli, B. subtilus, S. serevisiae, S. pombe, H. polymorpha, P. pastoris*, an insect cell, a plant cell or a mammalian cell, but not limited thereto.

In more preferred embodiment, the RNA molecule is artificially over-expressed by constructing a vector expressing said RNA molecule and then introducing the vector into a host cell.

In a preferred embodiment, the method of the present invention comprised the steps of:

1) constructing an expressing vector comprising a polynucleotide encoding a target protein wherein the target protein is expressed as a fusion protein with an RNA-binding protein;

2) constructing an expression vector comprising a polynucleotide encoding an RNA molecule capable of binding to the RNA-binding protein; and 3) cotransforming a host cell with the expression vectors prepared in step 1 and 2.

In addition, the present invention provides a method for producing a target protein having improved solubility and folding efficiency using an RNA molecule as a molecular chaperone, comprising expressing the target protein linked to an RNA-binding protein, and forming an ribonucleotide protein (RNP) complex between an RNA molecule and the RNA-binding protein.

In an embodiment, the method of the present invention comprises the following steps:

1) constructing a expression vector comprising a polynucleotide encoding a target protein linked to an RNA-binding protein;

2) transforming a host cell with the expression vector;

3) culturing the transformed host cell in an appropriate medium under the condition that an RNA molecule interacts with the RNA-binding protein linked to the target protein;

4) recovering the target protein from the culture medium or cell lysate.

Since solubility of proteins is largely dependent on their average net charges and folding speeds, it is hard to increase solubility of proteins only by artificially modifying the folding speeds of proteins. Based on the fact that RNA molecules having high solubility in vivo and highly negative net charges, in the present invention, a target protein is expressed as a fusion protein employing an RNA-binding protein as a fusion partner. The fusion protein is allowed to bind an RNA molecule, where the RNA molecule present at a stable state supplies a strong negative charge, thereby increasing an average net negative charge of the RNP complex formed between the RNA and the target protein. The charge-charge repulsion among negatively charged RNP complex discourages intermolecular interactions among RNP complex. This prevents intermolecular aggregation leading to inclusion bodies and favors intra-molecular folding of the target protein into functional form that leads to increased solubility of the target protein.

The RNA molecule may be naturally present in cells, or an artificially co-expressed RNA molecule capable of binding to the RNA-binding protein. Such co-expression of the RNA molecule may be achieved by constructing a vector expressing the RNA molecule and then introducing the vector into a host cell to over-express the RNA molecule.

The method for producing a target protein having improved solubility and folding efficiency comprises following steps:

1) constructing an expression vector encoding a fusion protein using a target protein and an RNA-binding protein;

2) constructing an expression vector expressing an RNA molecule capable of binding to the RNA-binding protein fused with the target protein; and 3) cotransforming a host cell with the expression vectors prepared in steps 1 and 2.

Alternatively, the method for producing a target protein having improved solubility and folding efficiency comprises following steps:

1) constructing a co-expression vector encoding both a target protein linked to an RNA-binding protein and an RNA molecule capable of binding to the RNA-binding protein; and 2) transforming a host cell with the co-expression vector prepared in the step 1.

Alternatively, the method for producing a target protein having improved solubility and folding efficiency comprises following steps:

1) constructing an expression vector encoding a target protein linked to an RNA-binding protein that interacts with RNA resident in the host cell; and 2) transforming a host cell with the expression vector prepared in the step 1.

The RNA molecule may be selected from the group consisting of tRNA, mRNA, rRNA, nuclear RNA, non-coding RNA, viral RNA, and ribo-polynucleotides artificially prepared by genetic recombination techniques.

The RNA-binding protein means a protein or polypeptide capable of binding to an RNA molecule. It comprises full-length RNA-binding proteins such as aminoacyl-tRNA synthetases, ribosomal proteins, mRNA binding proteins, non-coding RNA binding proteins, viral proteins having RNA-binding capacity and proteins associated with cellular RNA processing and turnover. In addition, it further comprises domains or minimal polypeptides or derivatives thereof.

Preferably, the RNA-binding protein is a protein selected from the group consisting of C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain of the aforementioned proteins.

Further, the present invention provides a method for producing a target protein having improved solubility and folding efficiency in intact form comprises following steps:

1) constructing a first gene construct comprising a gene encoding a fusion protein serially consisting of an RNA-binding protein, a recognition sequence for a sequence-specific protease and the target protein;

2) constructing a second gene construct comprising a gene encoding the sequence-specific protease;

3) co-transforming a host cell with the first gene construct and the second gene construct;

4) culturing the co-transformed host cell in an appropriate culture medium under the condition that the sequence specific protease cleaves the fusion protein and releasing the target protein in intact form; and 5) recovering the target protein from the culture media or cell lysate.

In an embodiment, the RNA-binding protein is a protein capable of binding to an RNA molecule, that is, a domain or polypeptide binding to an RNA molecule, or a derivative of a protein binding to an RNA molecule.

In a more preferred embodiment, the RNA-binding protein is selected from the group consisting of aminoacyl-tRNA synthetases, ribosomal proteins, mRNA binding proteins, non-coding RNA binding proteins, viral proteins having RNA-binding ability and proteins associated with cellular RNA processing and turnover, or a polypeptide corresponding to an RNA-binding domain (RBD) of the aforementioned proteins. More preferably, the RNA-binding protein is selected from the group consisting of C5 protein of ribonuclease P (RNase P), Ffh protein of signal recognition particle, NP protein of influenza virus, ribosomal S1 protein, ribosomal S4 protein, ribosomal S17 protein, *E. coli* DbpA, *E. coli* Hsp15, *E. coli* DnaK, mutant of DnaK, N-terminal domain of DnaK, murine Hsc70 and N-terminal domain of human lysyl-tRNA synthetase or a polypeptide corresponding to an RNA-binding domain of the aforementioned proteins.

In an embodiment, the sequence-specific protease is enterokinase, factor Xa or TEV protease, but not limited thereto.

In an embodiment, the first gene construct and/or the second gene construct further comprise promoter. In a more preferred embodiment, the first gene construct and/or the second gene construct further comprise inducible promoter. The inducible promoter is LacZ, T7 RNA promoter or arabinose promoter but not limited thereto.

In an embodiment, the host cell is *E. coli, B. subtilis, S. serevisiae, S. pombe, H. polymorpha, P. pastoris*, an insect cell, a plant cell or a mammalian cell, but not limited thereto.

Leading to the present invention, the intensive and thorough research into methods of improving solubility and folding of a target protein, conducted by the present inventors, resulted in the finding that RNA molecule could act as molecular chaperone and facilitate the folding of variety of target proteins in vivo if a target protein is expressed as a fusion protein linked to an RNA-binding module. When the RNA-binding module is placed at the N-terminus of the target protein, this module, upon binding with their cognate RNA, promotes the folding of downstream proteins in a cis-acting manner. The RNA binding-mediated protein folding is expected to proceed through charge-charge interactions. This novel mechanism of folding is fundamentally different and distinct from classic molecular chaperones. The molecular chaperones are proteins and assist folding by direct interaction with target proteins and shielding of hydrophobic residues of folding intermediates (Hartl, F. U. and Hayer-Hartl, M., Science, 295: 1852-1858, 2002).

Figure 1:
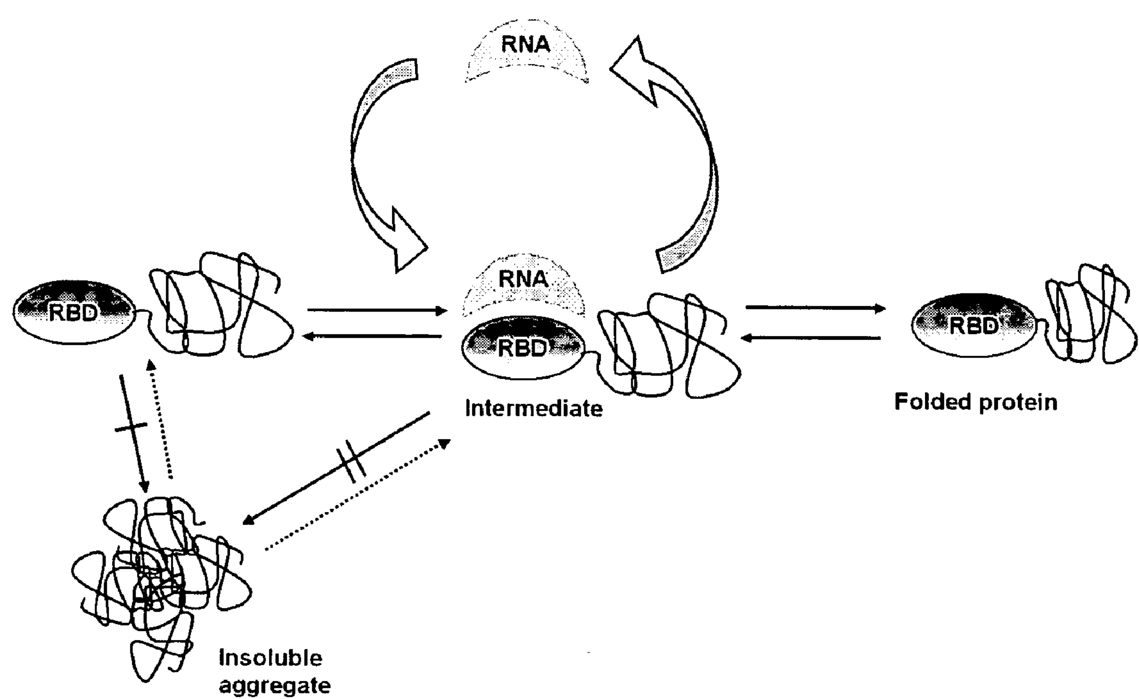
FIG. 1 is a schematic diagram for the concept of the present invention.

The present invention uses an RNA molecule as chaperone, which assists folding by charge-charge repulsion mechanistically distinct from the molecular chaperones. RNA is a polymer with highly negatively charged phosphate backbone. The RNA molecule, therefore, upon binding to RNA-binding protein fused to the target protein, is expected to increase significantly the overall net negative charge of the RNP complex. The electrostatic repulsion among RNP complex counteracts intermolecular hydrophobic interaction that normally leads to misfolded insoluble inclusion bodies and leads to accumulation of properly folded soluble proteins (See FIG. 1). Here, RNA functions as molecular chaperone that assists protein folding; folding of the target protein into functional form is expedited by the RNA that binds to the RNA-binding protein linked to the target protein. Since all different cells (e.g. *E. coli, B. subtilis, S. serevisiae, S. pombe, H. polymorpha, P. pastoris*, an insect cell, a plant cell or a mammalian cell, etc) share common cellular machineries for replication, transcription and translation, they contain mRNA, tRNA, rRNA, non-coding RNA along with proteins that interact with them for their function and turnover. Moreover, all viruses express proteins that interact with nucleic acids (DNA or RNA), either of viral or cellular origin to successfully infect host cell. RNA constitutes a major class of macromolecules inside cells (Ellis, R. J. *Trends Biochem. Sci.* 26; 597-604, 2001), and there are varieties of RNA binding proteins that generally exhibit significant non-specific affinity (Wang, C. C., Morales, A. J. and Schimmel, P. *J. Biol. Chem.* 275; 17180-17186, 2000). Therefore, the present invention that uses RNA as chaperone for enhancement of folding and solubility can be used in a variety of cells including *E. coli, B. subtilis, S. serevisiae, S. pombe, H. polymorpha, P. pastoris*, an insect cell, a plant cell or a mammalian cell, etc.

The present invention applies to folding of a variety of proteins of various origins including human and is expected to bring tremendous impact on production and structure-function analysis of human proteins, target identification and validation for new drug targets in the post-genome era.

DNA or RNA molecules have a net negative charge due to oxygen molecules of phosphate groups in their backbone, and are thus highly soluble polymers. RNA molecules, in vivo, interact with a large number of proteins because of participating in replication, transcription and translation. When a protein composed of 200 neutral amino acid residues forms a complex with an RNA molecule composed of 100 nucleotides, an average net charge of the protein is calculated to increase by about −0.2, where molecular weight of the RNA molecule is converted to number of amino acid residues by dividing the molecular weight of the RNA molecule by an average molecular weight of amino acids (100×330/110=300) on the assumption that solubility of nucleotides and amino acid residues per unit mass excluding charges is identical, and an average number of the RNP complex converted to amino acid number is 500. If such a negative net charge of the RNP complex is converted to amino acid number, the RNP complex is equivalent to a protein of 200 amino acid residues and additional 50 residues consisting of aspartate or glutamate.

When a protein is expressed as a fusion protein in which a target protein is linked to a protein having high affinity to DNA or RNA molecules (hereinafter, refer to as 'nucleotide binding domain'), the fusion protein forms a nucleic acid-protein complex by binding of the DNA or RNA molecule to the domain, and the strong negative charge of the DNA or RNA molecule changes an average net charge of the complex, thereby increasing its interaction with water, resulting in the increase of the solubility of the target protein (Reaction Formula 3). RNA molecules are more effective than DNA molecules in improving solubility of a target protein in terms of being present at a much higher amount, in much diverse conformation and being more widely present than DNA in the cell.

[Reaction Formula 3]

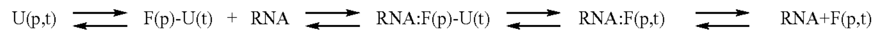

$$U(p,t) \rightleftharpoons F(p)\text{-}U(t) + RNA \rightleftharpoons RNA{:}F(p)\text{-}U(t) \rightleftharpoons RNA{:}F(p,t) \rightleftharpoons RNA + F(p,t)$$

wherein, U is an unfolded state; F is a folded state; p is a fusion partner; and T is a target protein. The novel method using RNA molecule as chaperone for folding and expression of RNA-binding protein-linked target proteins of the present invention has never been disclosed nor suggested before including WO 98/14591.

According to affinity of a protein to an RNA molecule, the protein binds to the RNA molecule either in an irreversible manner in which the protein strongly binds to the RNA molecule resulting in stable ribonucleoprotein (hereinafter, referred to as "RNP"), or in a reversible manner in which the proteins weakly bind to the RNA molecules resulting in unstable RNP. It is known that *E. coli* RNP molecules include ribosome, ribonuclease P (hereinafter, referred to as "RNase P") and signal recognition particle (hereinafter, referred to as "SRP"). Ribosomes are the largest RNP complexes among RNA-protein complexes identified until now.

Non-limiting examples of the protein binding to a target protein and having a binding affinity to an RNA molecule include the following proteins. RNase P, which is an endonuclease catalyzing cleavage of the 5' end of a tRNA precursor, consists of a catalytic RNA subunit (M1 RNA, 377 nucleotides) and C5 protein (119 amino acid residues) affecting stability and activity of RNase P (Gopalan et al., *J. Mol. Biol.*, 267: 818-829, 1997). The C5 protein may be used as a RNA-binding protein for linking target protein having valuable biological activity. SRP is known to induce translocation of proteins to the endoplasmic reticulum (ER) membrane in eukaryotic cells, and to target proteins to nascent inner membrane proteins to transport sites the inner membrane in *E. coli. E. coli* SRP consists of 4.5S RNA and Ffh protein, and the Ffh protein contains an RNA-binding protein ranging from 296 to 453 amino acid residues (Barty et al., *J. Mol. Biol.*, 307: 229-246, 2001).

The conventional fusion proteins using pro-sequences as fusion partners consist of only proteins. In contrast, the RNA-binding protein linked to a target protein of the present invention differs from the conventional fusion partners in terms of its ability to interact with RNA to form ribonucleoprotein (RNP) complex consisting of RNA molecule and protein.

In case of the conventional protein expression system using molecular chaperone proteins, in order to express a target protein in an active form, the chaperone should be additionally introduced into a host cell transformed with the target protein, or expressed separately along with the target protein, and the chaperone proteins facilitates folding of target protein in a trans-acting manner. In contrast, the method of the present invention is advantageous in that a target protein linked and an RNA-binding protein is expressed as one protein, and the RNA-binding protein, upon binding with RNA promotes folding of the down-stream target protein in a cis-acting manner resulting in production of an RNA-binding protein-target fusion protein in a soluble and folded into active from.

In addition, in the case of the conventional protein expression system using ribosome or 23S RNA, ribosome or 23S RNA is used in converting a target protein expressed in an inactive form to an active form using in vitro refolding method (Das et al., *Eur. J. Biochem.* 235; 613-621, 1996). The process requires initial unfolding of target proteins in the presence of chemicals such as urea or guanidium HCl, followed by refolding by removing or diluting the chemical agent. The process is time-consuming, laborious, environmentally unfriendly, and requires bulky instruments such as refolding tanks. Moreover, the 23 rRNA does not provide efficient interaction with most proteins and therefore the repertoire of proteins that would be folded by this process is extremely limited.

In contrast, the method of the present invention is distinguishable from the conventional method in terms of expressing in vivo a target protein in an active form from the beginning, without requirement of chemicals nor requiring laborious refolding process.

An RNA-protein complex is stably formed, in which a protein binds to an RNA molecule with a strong association constant, and the binding is in equilibrium. The RNA-protein complex is advantageous in terms of enabling solubility and folding efficiency of the protein fused to an RNA-binding protein to increase by the RNA molecule's properties of having a net negative charge and high solubility. That is, intermolecular aggregation of the fusion proteins is inhibited by repulsion of negative charges of the fusion proteins, resulting in that each of the fusion proteins is present in a separate form, and the fusion proteins are highly soluble in an aqueous environment by interaction between the net charges and water molecules. The RNA molecule binding to the RNA-binding protein serves as a molecular chaperone by inducing the protein to fold into its active form. Herein, factors that affect efficiency of the RNA-mediated protein folding include the affinity between the RNA-binding protein and the RNA molecule. Therefore, the present invention clearly suggests that an RNA-binding protein with increased affinity towards an RNA molecule could greatly increase the folding efficiency and soluble yield of the target protein as compared to an RNA-binding protein with lower affinity. With respect to the function and efficiency, the RNA molecule as a molecular chaperone, mediated by the charge-charge repulsion, is distinguished from conventional fusion proteins such as the one linked to a soluble fusion partner or co-expression of chaperone proteins that mediate protein folding by protein-protein interaction.

The present invention will be explained in more detail with reference to the following examples. However, the following examples are provided only to illustrate the present invention, and the present invention is not limited to them.

EXAMPLE 1

Preparation of Expression Vectors Encoding RNA-Binding Proteins to be Linked to Target Proteins Expression vectors expressing RNA-binding proteins to be fused to target proteins forming RNP complexes with tRNA, mRNA or rRNA were constructed. In detail, the following proteins were selected as RNA-binding proteins to link target proteins: *E. coli* lysyl tRNA synthetase (hereinafter, referred to as "lysRS"), tyrosyl tRNA synthetase (hereinafter, referred to as "tyrRS"), tryptophan tRNA synthetase (hereinafter, referred to as "trpRS"), *E. coli* rRNA binding proteins S1, S4 and S17, *E. coli* Hsp 15 and DbpA, Ffh protein of *E. coli* signal recognition particle (SRP), C5 protein of RNase P and influenza A virus (WSN/3/33) nucleoprotein (NP).

Figure 2:
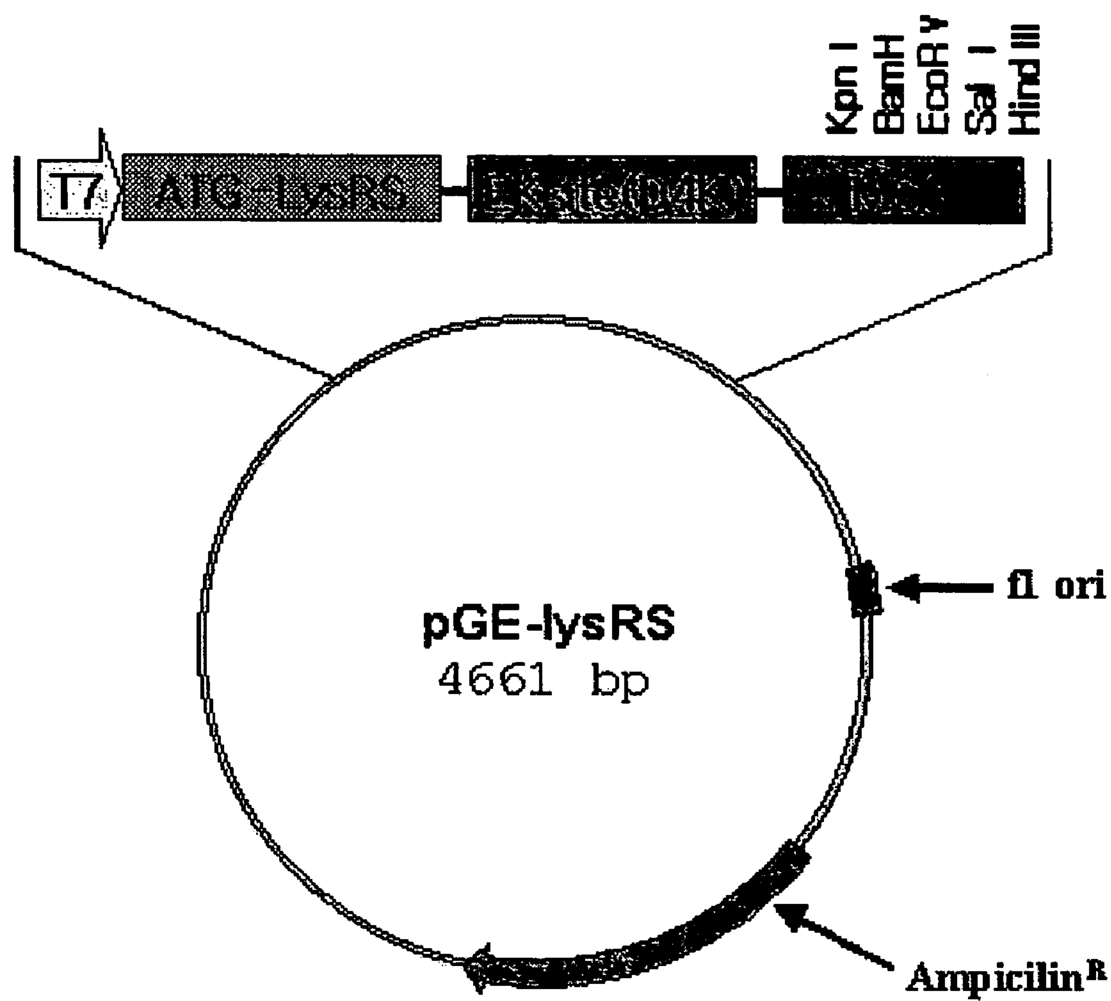
FIG. 2 is a diagrammatic representation of a pGE-lysRS vector.

First, PCR was carried out using genomic DNA obtained from JM109 cells (*Gene,* 1985, 33, 103-119) as a template and primers designated SEQ ID NO: 1 and SEQ ID NO: 2. The resulting PCR product 'lysRS' was cloned to a pGEMEX-ΔNdeI vector, which was prepared by removing a Nde I site at the 3251 position among two NdeI sites present in the pGEMEX-1 vector (Promega), giving a pGE-lysRS expression vector (FIG. 2). In addition, expression vectors carrying genes encoding other aforementioned proteins except NP protein were prepared by PCR using primers designated with the SEQ ID NOs listed in Table 1, below, according to the same method as in constructing the expression vector carrying the lysRS gene. An expression vector expressing NP protein of influenza virus was prepared by PCR using plasmid DNA from a pIVA-NP vector having a gene encoding NP protein, in which the gene is positioned at an EcoR I site of pUC19 vector (*Gene,* 1985, 33, 103-119) and under the regulation of T7 promoter, as a template, and primers designated SEQ ID NO: 21 and SEQ ID NO: 22, and then inserting the resulting amplified product into Nde I/Kpn I sites of the pGE-lysRS vector, giving a PGE-NP vector. In order to compare effect of the fusion partners on solubility and folding efficiency of target proteins with proteins not binding to RNA molecules, a vector expressing *E. coli* maltose binding protein (MBP) that is known to not bind to RNA molecules was prepared according to the same method as described above, thus yielding a pGE-MBP vector.

TABLE 1

| Genes | Primers | Expression vectors |
|---|---|---|
| tyrRS | SEQ ID NOs: 3 and 4 | pGE-tyrRS |
| trpRS | SEQ ID NOs: 5 and 6 | pGE-trpRS |
| S1 | SEQ ID NOs: 7 and 8 | pGE-S1 |
| S4 | SEQ ID NOs: 9 and 10 | pGE-S4 |
| S17 | SEQ ID NOs: 11 and 12 | pGE-S17 |
| Hsp15 | SEQ ID NOs: 13 and 14 | pGE-Hsp15 |
| DbpA | SEQ ID NOs: 15 and 16 | pGE-DbpA |
| Ffh | SEQ ID NOs: 17 and 18 | pGE-Ffh |
| C5 | SEQ ID NOs: 19 and 20 | pGE-C5 |
| NP | SEQ ID NOs: 21 and 22 | pGE-NP |
| MBP | SEQ ID NOs: 23 and 24 | pMBP |

EXAMPLE 2

Evaluation of Effect of RNA Binding Domains on the Solubility of a Target Protein In order to investigate effect of RNA-binding proteins from various sources on solubility of a target protein, protease of tobacco etch virus (hereinafter, referred to as “TEV”) was used as a target protein, and fused with each RNA-binding protein. In detail, PCR was carried out using pRK793 plasmid (*Protein Engineering,* 14; 993-1000, 2001) as a template and primers designated SEQ ID NO: 25 and SEQ ID NO: 26. The amplified PCR product was inserted into each of the vectors prepared in Example 1, pGE-lysRS, pGE-Hsp15, pGE-Ffh, pGE-C5, pGE-NP and pGE-MBP. The resulting expression vectors were designated as “plysRS-TEV”, “pHsp15-TEV”, “pFfh-TEV”, “pC5-TEV” and “pNP-TEV”.

Then, each of the expression vectors was introduced into *E. coli* HMS174(DE3)plysE (Novagen, USA). Single colonies were inoculated in 2 ml of LB medium containing ampicillin of 50 μg/ml and chloramphenicol of 30 μg/ml, followed by incubation at 37° C. overnight. The cultured cells were diluted in 20 ml of LB medium, and cultured until $OD_{600}$ reached 0.5. Thereafter, 1 mM IPTG was added to the culture medium, and the transformed cells were incubated at 37° C. or 27° C. for 5 hrs to express the recombinant proteins. After collecting 10 ml from the resulting cultured medium, the harvested cell pellet was supplemented with 0.3 ml of PBS and sonicated using a sonifier. 50 μl of the total cell lysates was mixed with 2×SDS buffer, and the remainder of cell lysate was centrifuged at 13,000 rpm for 12 min, thus yielding a supernatant. Also, the pellet was suspended in 250 μl of PBS. 50 μl of each of the supernatant and the pellet was mixed with 50 μl of 2×SDS buffer. After being boiled at 100° C., the mixtures were electrophoresed on a SDS-PAGE gel, and the separated proteins were stained with Coomassie blue.

Figure 3:
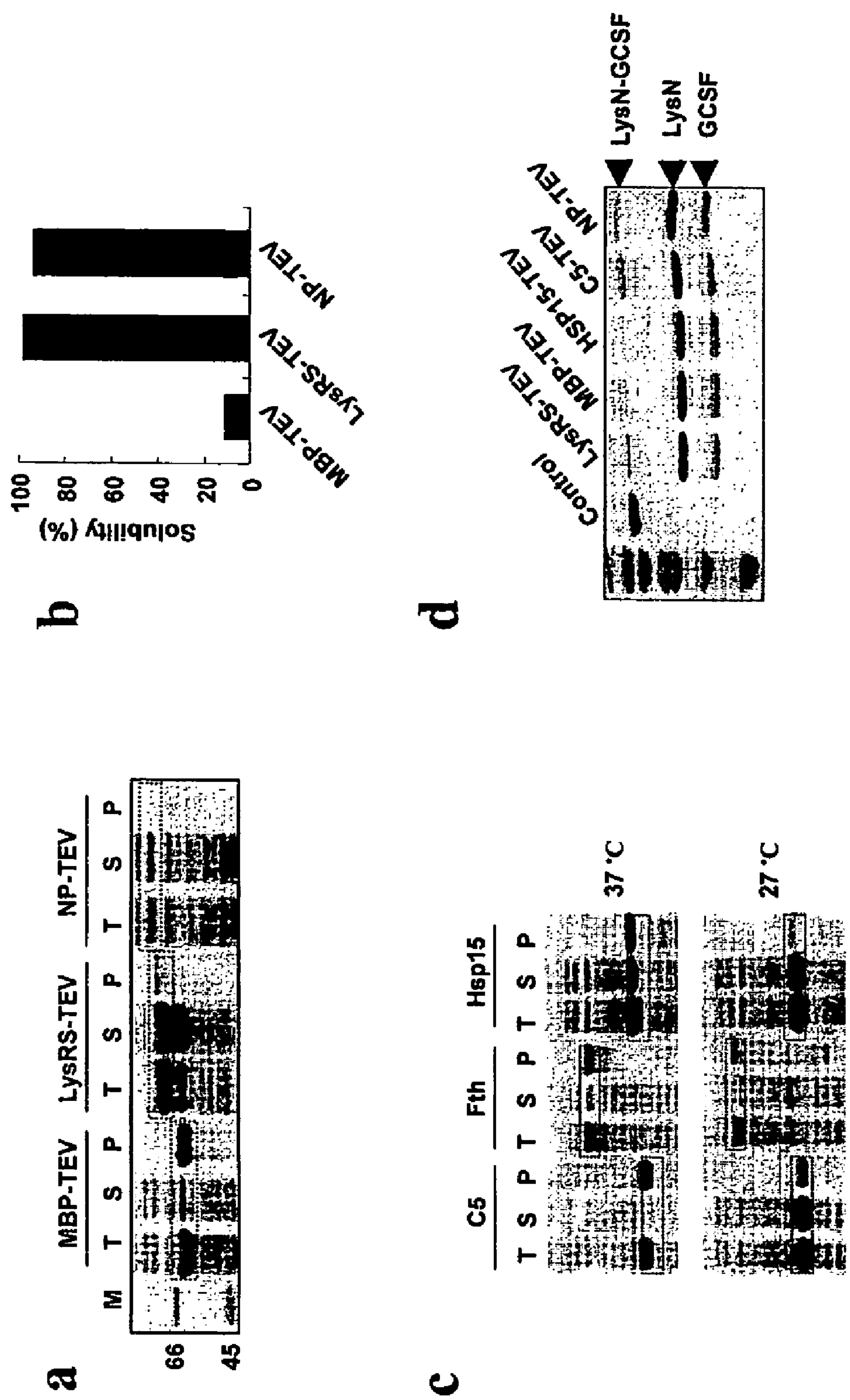
FIG. 3*a* is a photograph showing results of SDS-PAGE analysis for solubility of fusion proteins obtained by expressing a target protein as a fusion protein at 37° C.
FIG. 3*b* is a graph showing same result with FIG. 3*a*.
FIG. 3*c* is a photograph showing results of SDS-PAGE analysis for solubility of fusion proteins (C5, Ffh and Hsp 15 fused with LysRS, respectively) at 37° C. and lower temperature (27° C.)
FIG. 3*d* is a photograph showing that various fusion proteins fused with TEV have intact TEV protease activities.

As a result, LysRS- and NP-fused TEV protease were predominantly expressed as a soluble form (≧90%) at 37° C., whereas MBP-fused TEV protease was marginally soluble (12%), indicating that both LysRS and NP are much superior to MBP for promoting the solubility of TEV protease (FIGS. 3*a* and 3*b*). Hsp15-TEV protease was expressed as a soluble form (40%) at 37° C., and the solubility was greatly increased at lower temperature (≧90%, FIG. 3*c*). Likewise, the solubility of C5-fused TEV protease was significantly increased at lower temperature. All TEV fusion proteins were functionally active as confirmed by the cleavage of fusion proteins containing TEV cleavage site at the linker region (FIG. 3*d*). The results indicate that RNA-binding proteins—RNA interaction generally exert potent solubility and folding enhancing ability to target proteins.

EXAMPLE 3

Comparison of Solubility-Enhancing Ability Between LysRS and its N-Terminal Domain (LysN)

LysN was known to exhibit strong solubility-enhancing ability as fusion partner (WO 98/14591). LysRS, as a whole RNA binding domain, binds to $tRNA^{Lys}$ much tighter than LysN (with approximately 10 fold higher affinity), and according to our rationale for folding efficiency in the present invention, LysRS is expected to serve as more efficient folding vehicle than LysN. Herein, the inventors observed that potential toxic effect associated with the expression of LysRS could be easily circumvented by simply changing *E. coli* hosts that are available from commercial sources. The aggregation-prone TEV protease was fused to the C-terminus of LysN and LysRS, respectively. The fusion proteins were expressed at 37° C. LysRS-TEV was expressed predominantly in a soluble form, whereas LysN-fused TEV protease was expressed almost completely in the form of inclusion bodies (FIG. 4*a*). The results demonstrated that LysRS is superior to LysN for promoting the solubility of proteins.

To further verify the robustness of LysRS in protein folding, various aggregation-prone proteins, including peptidylglycine α-hydroxylating monooxygenase (PHM), granulocyte colony stimulating factor (GCSF) and green fluorescent protein (GFP) were further compared. Vectors encoding LysRS fused to said aggregation-prone proteins were prepared by same process with that of Example 2 except primers. In addition, vectors encoding LysN fused to said aggregation-proteins were prepared by process of WO 98/14591 and Example 2. The fusion proteins were expressed at 37° C. LysRS-fused PHM, GCSF, and GFP were expressed predominantly in a soluble form, whereas LysN-fused PHM, GCSF, and GFP were expressed almost completely in the form of inclusion bodies or marginally soluble (FIG. 4*b*). After fractionation of proteins on SDS-PAGE, the relative solubility of each expressed proteins were estimated by densitometric scanning of proteins bands of both soluble (S) and insoluble pellet (P) fractions. The solubility of LysN-fused TEV, PHM, GCSF, and GFP was approximately 5%, 2%, 44%, and 15%, respectively. In contrast, the solubility of LysRS-fused corresponding proteins was approximately ≧90%, 75%, ≧93%, and ≧92%, respectively, suggesting that the relative solubility was increased by 18, 38, 2 and 6 fold, for each target protein. The results firmly demonstrate that LysRS is much superior to previously described LysN for promoting the solubility of aggregation-prone proteins.

EXAMPLE 3

CIP (Controlled Intracellular Processing) of Fusion Proteins with NP-TEV Protease To obtain mature proteins of interest, the RNA-binding protein-target fusion protein, after purification from the expression host, must then be treated in vitro with sequence-specific proteases such as enterokinase, thrombin, factor Xa, or TEV protease. However, these procedures are usually time-consuming and labor-intensive. To overcome these problems and simplify the overall process for protein production, we constructed an in vivo cleavage system where the expression of fusion protein and the cleavage by site-specific protease occur simultaneously inside the cell (controlled intra-cellular processing). For this, functionally active TEV protease is expressed by autocatalytic cleavage of RBP-TEV protease at the linker region containing the TEV recognition site. Here, the TEV protease was fused to the C-terminus of NP. The DNA fragments encoding arabinose promoter was obtained by PCR amplification using pBAD/gIII vector (Invitrogen, USA) as a template and primers having nucleotide sequence of SEQ ID NOs: 27 (5' CCG ATC GCG AAA ACC AAT TGT CC 3') and 28 (5' TAT CCC CGA GTA CGT GGT TAA CTT CCT CCT GTT AGC C3'). DNA fragments cleaved with Nru I/Ava I was ligated into Nru I/Ava I sites of plysE vector (Novagen, USA), yielding plysE-Bad. Then, the DNA fragments encoding NP and TEV protease, respectively, were obtained by PCR amplification using the following primer sets. The primers used for NP gene are 5' GCA AGT TAA CAT GGC GTC TCA AGG 3' (SEQ ID NO: 29) and 5' TTT CGG ATC CGG TAC CAT TGT CGT ACT CC 3' (SEQ ID NO: 30). The primers for TEV protease are 5' AGA GGA GTA CGA CAA TGG TAC CGG ATC C3' (SEQ ID NO: 31) and 5' TGT CCC CGA GTT ATT AGC GAC G 3' (SEQ ID NO: 32). Two amplified DNA fragments were fused by overlapping PCR. The resulting DNA fragments were cleaved with Hpa I/Ava I and ligated into Hpa I/Ava I sites of plysE-Bad, yielding pNPTEV in which TEV protease recognition sites are inserted between NP and TEV protease.

*E. coli* cells (HMS174(DE3)) were co-transformed with pLysRS-Parkin encoding LysRS-Parkin which carries TEV linker region and pNPTEV. pLysRS-Parkin was constructed as follows: DNA fragments encoding Parkin were amplified using the following primers: the forward primer: 5'_ACG TGG ATC CAT GAT AGT GTT TGT C 3' (SEQ ID NO: 33), the reverse primer: TGC AGT CGA CTT ACT ACA CGT CGA ACC AG 3' (SEQ ID NO: 34). The amplified fragments were cloned into BamH I/Sal I sites of pGELysRS, yielding the plasmid pLysRS-Parkin. Prkin is one of the key proteins related to the progression of Parkinson's disease.

Figure 4:
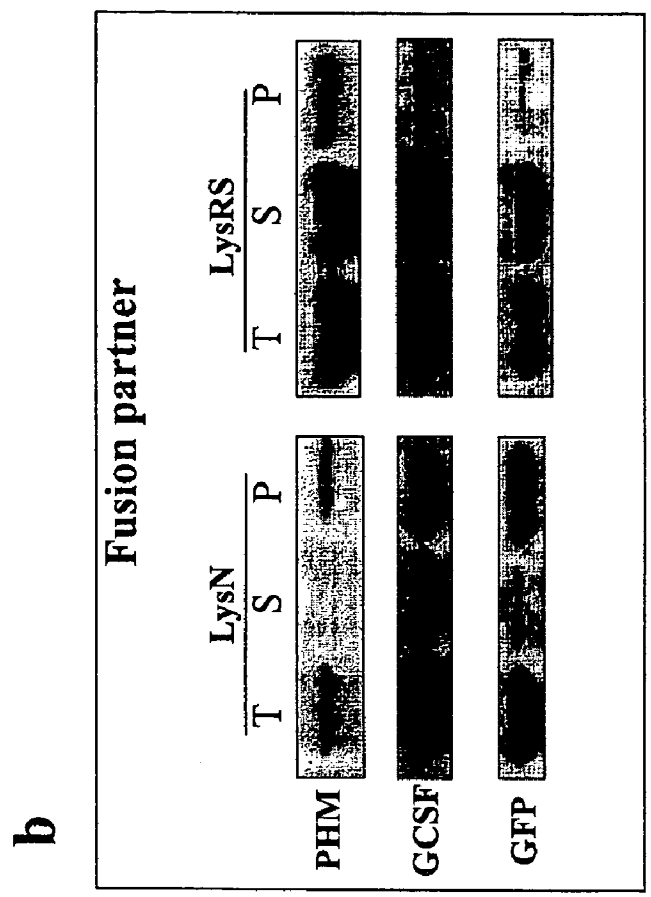
Figure 4:
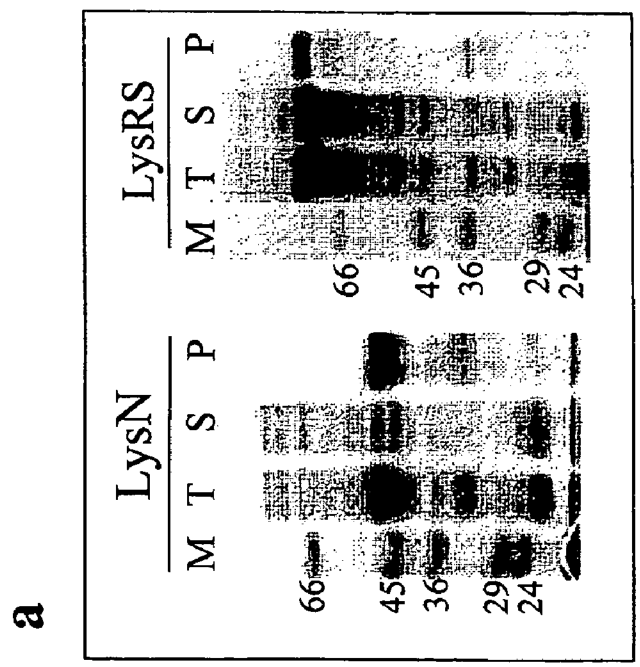

The transformed *E. coli* cells expressing the NP-TEV and LysRS-Parkin proteins were induced with two different inducers, 1 mM IPTG and 0.2% arabinose, respectively, and further cultured at 37° C. for 6 h. Soluble TEV protease was produced from NP-TEV protease fusion protein through the autocatalytic cleavage (FIG. 5 lane 8-9), and this TEV exerted the cleavage of the co-expressed LysRS-Parkin fusion protein to yield the mature Parkin protein in vivo (FIG. 4 lane 15-16).

EXAMPLE 4

DnaK as a Solubility-Enhancing RNA-Binding Protein

DnaK, one of the well-known molecular chaperones, exhibit a RNA-binding property. Thus, we tested whether DnaK could be a useful fusion partner for enhancing the solubility of fusion proteins. DNA fragments encoding DnaK without translational codon were obtained from *E. coli* genomic DNA by PCR amplification using the following primers. The primers are 5' GTC ACG CAT ATG GGT AAA ATA ATT GGT ATC 3' (SEQ ID NO: 35) and 5' GTC ACG GGT ACC TTT TTT GTC TTT GAC TTC TTC AAA TTC AGC GTC3' (SEQ ID NO: 36). The resulting DNA fragments were cleaved with Nde I/Kpn I was ligated into the same restriction sites of pGE-LysRS, yielding pDnaK fusion vector. To investigate the potential roles of DnaK as fusion partner, three aggregation-prone proteins, including human granulocyte colony-stimulating factor (GCSF), green fluorescent protein (GFP), and TEV protease were fused to the C-terminus of DnaK, respectively. All DnaK-fused proteins were expressed predominantly as a soluble form at 37° C. (FIG. 6), indicating that DnaK exhibit strong solubility-enhancing ability as a fusion partner.

It is known that DnaK acts as a molecular chaperone by recognizing exposed hydrophobic sites of normative proteins. However, our chaperone concept in the present invention is based on the RNA-binding and resulting charge effect. From this perspective, the recognition of hydrophobic sites could exhibit negative effects on the ability of DnaK as fusion partner. Therefore, a DnaK mutant, DnaK-V436F in which valine is substituted with phenylalanine at 436 residue, was tested. The DnaK-V436F was previously reported to exhibit only marginal peptide-binding ability. The DnaK-V436F was constructed by overlapping PCR mutagenesis using the following primers corresponding to the mutation site. The primers are 5' GAA GAC AAC CAG TCT GCG TTC ACC ATC CAT GTG CTG CAG GGT 3' (SEQ ID NO: 37) and 5' CAG CAC ATG GAT GGT GAA CGC AGA CTG GTT GTC TTC AGC 3' (SEQ ID NO: 38). The resulting plasmid was named pmDnaK. The target proteins, GCSF, GFP, and TEV protease, respectively, were fused to the C-terminus of DnaK-V436F. All DnaK-V436F fusion proteins were expressed as a soluble form at 37° C. (FIG. 7). Moreover, DnaK-V436F is more effective than DnaK in solubility enhancing activity, as shown in the case of TEV protease (see and compare lanes 8-10 in FIG. 6 and lanes 8-10 in FIG. 7).

The N-terminal domain of DnaK (Do1) exhibits RNA-binding property. Thus, we tested whether Do1 alone, as a distinctive RNA-binding protein, exhibit solubility-enhancing ability. DNA fragments encoding Do1 without translational stop codon were obtained by PCR amplification using the following primers, yielding a recombinant expression vector, pDo1. The primers are the sense primer used in DnaK (SEQ ID NO: 33) and 5' GTC ACG GGT ACC CTA ACC AGT CAG AAC ACC ACC CTG 3' (SEQ ID NO: 39). The GCSF, GFP, and TEV protease were fused to the C-terminus of Do1. The Do1 fusion proteins were expressed predominantly as soluble form (FIG. 8), indicating that Do1, as an independent RNA-binding protein, also exhibit solubility-enhancing ability.

EXAMPLE 5

N-Terminal Domain of Human lysyl-tRNA Synthetase as Solubility-Enhancing RNA-Binding Protein The N-terminal domain of human LysRS (1-71 residues; $hLRS_{1-71}$) exhibits RNA-binding ability. Thus, we tested whether this domain exhibits solubility-enhancing ability as a fusion partner. A polynucleotide encoding the $RBD_{1-71}$ was obtained by overlapping PCR using 4 primers. The used primers are as follow: 5' GTC ACG ATT AAT ATG GCG GCC GTG CAG GCG GCC GAG GTG AAA GTG GAT GG 3' (SEQ ID NO: 40), 5' CAG CGA GCC GAA CTC TGC TAC TTT CTT CTC AGC TTT CAG GCG TCT CTT CAG CTC ATT CTT GTC CAG TTT CGG CTC GC 3' (SEQ ID NO: 41), 5' AGT AGC AGA GAA GGA GGC CAA ACA GAA AGA GCT CAG TGA GAA ACA GCT AAG CCA AGC CAC TGC TG 3' (SEQ ID NO: 42), and 5' GTC ACG GGA TCC CAC GCT CTC TTC CTC AGG ACC CAC ACC ATT ATC AGT GGT GTG GTT GGT GGC AGC AGC AGT GGC 3' (SEQ ID NO: 43). To increase the yield of translation efficiency, the N-terminal regions (1-7 residues) of *E. coli* LysRS were added to $RBD_{1-71}$. A polynucleotide encoding $RBD_{1-17}$ was obtained by PCR amplification using the primer of SEQ ID NO: 41 and 5' GTC ACG ATT AAT ATG TCT GAA CAA CAC GCA CAG GCG GCC GTG CAG GCG GCC GAG 3' (SEQ ID NO: 44). The resulting DNA fragments were cleaved with Ase I/BamH I, and then ligated into Nde I/BamH I sites of pGE-LysRS, yielding a recombinant expression vector, $pRBD_{1-71}$ fusion vector.

To test $RBD_{1-71}$ as an independent RNA-binding protein, GCSF and EAST6 (*Mycobacterium tuberculosis* early secretory antigen) were fused to the C-terminus of $hLRS_{1-71}$. Primers used for PCR amplification of EAST6 are 5' ATC ATG ACA GAG CAG CAG TGG AAT TTC GCG 3' (SEQ ID NO: 45) and 5' GTC ACG GGA TCC CTA TGC GAA CAT CCC AGT GAC 3' (SEQ ID NO: 46). The $hLRS_{1-71}$-GCSF and $hLRS_{1-71}$-EAST6 were expressed predominantly as soluble form at 30° C. (FIG. 9). The results showed that despite its small size, $hLRS_{1-71}$ exhibits potent solubility-enhancing ability when linked to target protein.

EXAMPLE 6

Murine Hsc70 as Solubility-Enhancing RNA-Binding Protein

Previously, the use of fusion proteins for production of specific antibodies suffered from a major drawback. Since the fusion partner of target origin is immunogenic, the immunization with the whole fusion protein would lead to generation of antibodies against the fusion partner as well as against the target protein. The lack of specificity would compromise the utility of antibodies for diagnostic, prophylactic or therapeutic applications. In contrast, fusion with proteins of murine origin could be very useful for production of mono-specific or monoclonal antibodies against target proteins from mouse. The fusion domain of murine origin is not immunogenic in mouse, and therefore, classic immunization of mice with the mHsc70 fusion protein would lead to generation of specific antibodies against the target protein. Alternatively the same fusion protein could be used for the generation of monoclonal antibodies by hybridoma approach.

For this purpose, we selected murine Hsc70 (mHsc70) protein as a fusion partner for soluble expression of target proteins and its use for generation of specific antibodies. The mHsc70 is known to bind RNA, and based on the technical concept of the present invention, fusion of target proteins to mHsc70 would lead to soluble expression of the target proteins.

A polynucleotide encoding murine Hsc70 was obtained by PCR amplification using FastClone PCR-Ready cDNA as template and the following primers. The primers are 5' CGG TCA CGC ATA TGT CTA AGG GAC CTG CAG TTG GCA TTG ATC TCG GC 3' (SEQ ID NO: 47) and 5' AGT GAC GGT ACC CTG AAA ATA CAG GTT TTC GCC GCT GTC ATC GTC ATC GTC ATC ATC CAC CTC TTC AAT GGT GGG GCC 3' (SEQ ID NO: 48). The amplified DNA fragments were cleaved with Nde I/Kpn I, and then ligated into the same restriction sites of pGE-LysRS, yielding a recombinant expression vector, pmHsc70.

To test mHsc70 as a fusion partner, AGR2 human anterior gradient 2 homolog (AGR2) and human ribosomal protein L36A (RPL36A) were fused to mHsc70, respectively. Primers used for AGR2 are 5' GTC ACG GGA TCC ATG GAG AAA ATT CCA GTG 3' (SEQ ID NO: 49) and 5' GTC ACG GTC GAC CAA TTC AGT CTT CAG 3' (SEQ ID NO: 50). Primers for RPL36A are 5' GTC ACG GAT ATC ATG GTT AAC GTC CCT AAA 3' (SEQ ID NO: 51) and 5' GTC ACG GTC GAC GAA CTG GAT CAC TTG GCC 3' (SEQ ID NO: 52). Polynucleotides encoding AGR2 and RPL36A were cloned into BamH I/Sal I and EcoR V/Sal I sites of pmHsc70, respectively. The mHsc70-AGR2 and mHsc70-RPL36A fusion proteins were expressed predominantly as soluble form at 37° C. (FIGS. 10*a* and 10*b*). The results showed that mHsc70 could be a useful fusion partner for soluble expression of target proteins in *E. coli.*

EXAMPLE 7

RNA-Mediated Protein Folding of LysRS In Vitro

It was demonstrated in Examples 3-6 that binding of RNA molecules in vivo to RNA-binding protein increases solubility of target proteins. In this test, the effect of such binding of RNA molecules on protein refolding to an active form was investigated, as follows: To investigate the effect of binding of RNA to RBD-harboring proteins on the folding of whole proteins, in vitro refolding of LysRS was performed by monitoring the activity of refolded LysRS by aminoacylation assay. The refolding of LysRS was conducted as follows: The purified LysRS with 6 consecutive histidine residue at its C-terminus was denatured in 6 M guanidine-HCl, 1 mM DTT, and 20 mM Tris-HCl (pH 7.8), to a final concentration of 1.3 μM for 2 h at 37° C. The denatured proteins were 50 fold diluted into the refolding buffer containing 20 mM Tris-HCl (pH 7.8), 1 mM DTT, 50 mM NaCl, 1 mM $MgCl_2$, and various RNA (2 μM or equivalent to 2 μM *E. coli* $tRNA^{Lys}$) and incubated for 1.5 h at 25° C. The enzyme activity of refolded LysRS was analyzed by aminoacylation assay of LysRS. The refolding mixture was 10 fold diluted into the aminoacylation assay buffer (total volume of 100 μl) containing 20 mM Tris-HCl (pH 7.8), 150 mM KCl, 2 mM ATP, 0.1 mM EDTA, 7 mM $MgCl_2$, 1 μCi of L-[$^{14}$C]-lysine, and 3.7 μM $tRNA^{Lys}$ at 30° C. At different time intervals, 10 μl of reaction mixture was mixed with the same volume of 10% (w/v) ice-cold trichloroacetic acid, placed on ice for 10 min. The precipitates were filtered through Whatman No. 2 filter paper, and washed once with 95% ethanol, followed by air drying. The bound [$^{14}$C]-lysine was determined with liquid scintillation counter.

The results showed that the folding of LysRS into functionally active form was stimulated about 100-150% by the presence of its cognate $tRNA^{Lys}$ as compared to controls without RNA (FIG. 11). Low, but detectable level of stimulation by yeast $tRNA^{Phe}$ may be due to non-specific interactions among non-cognate tRNAs and LysRS. This result suggests that the binding with cognate $tRNA^{Lys}$ is important for the promotion of the folding of LysRS in vitro, validating the novel concept of using RNA molecule as chaperone that expedites folding of RNA-binding protein-target fusion protein.

EXAMPLE 8

The Effect of an RNA Molecule on Folding Efficiency of a Target Protein when RNA-Binding Protein-Target Fusion is Allowed to Bind to the RNA Molecule A fusion protein was used, which was prepared by linking a luciferase gene to a gene encoding LysN, which is the N-terminal domain of LysRS specifically binding the anticodon of lysine tRNA. The luciferase gene was amplified by PCR using pGL2-Basic vector (Promega) as a template and primers designated SEQ ID NO: 53 and SEQ ID NO: 54. The amplified luciferase gene was inserted into BamH I/Hind III sites of pGE-lysN vector (Korean Pat. NO: 203919), the resulting vector was designated as "pLysN-firefly luciferase". Thereafter, the pLysN-firefly luciferase vector was introduced into HMS174(DE3)plysE cells to express LysN-luciferase fusion protein, where the fusion protein was expressed as inclusion bodies. After being washed with PBS containing 200 mM NaCl, 1 mM EDTA and 1% triton X-100 three times, and with distilled water three times, the inclusion bodies were solubilized in PBS containing 6 M guanidium HCl and 2 mM DTT, and then diluted with 100 times of a refolding buffer containing 20 mM KCl, 3 mM $MgCl_2$, 2 mM DTT and 0.1 mg/ml BSA. The diluted solution was analyzed for luciferase activity using a firefly luciferase assay kit (Promega) at 30° C. at 10, 20, 40 and 80 min in the presence of lysine tRNA or phenylalanine tRNA. Herein, phenylalanine tRNA was used as a control because the anticodon of phenylalanine tRNA is opposite to the lysine codon, and the anticodon of lysine tRNA is required for recognition by LysN.

As a result, when the LysN-luciferase fusion protein was present with lysine tRNA, luciferase activity was higher than in the presence of phenylalanine tRNA (FIG. 12), indicating that refolding of the luciferase enzyme to an active form takes place. These results demonstrate that binding of RNA molecules to the fusion partners leads to increase folding efficiency and solubility of target proteins.

In addition, despite the fact that LysRS is known to bind to lysine tRNA, in order to investigate whether the LysRS-PHM fusion protein actually binds to lysine tRNA, and such binding induces refolding of the target protein into an active form, binding of LysRS-PHM to lysine tRNA was estimated. RNA binding was analyzed by the method for analyzing tRNA synthetase activity, that is, the aminoacylation charging assay. After isolating LysRS protein and LysRS-PHM fusion protein from cells (FIG. 13*a*), their RNA binding activity was evaluated, where each of 0.4 μM LysRS and 0.4 μM LysRS-PHM was added to 100 μl of a buffer containing 150 mM KCl, 2 mM ATP, 0.1 mM EDTA, 7 mM $MgCl_2$ and $^{14}C$-labelled lysine, and incubated at 37° C. 10 μl samples were collected from the reaction solution at 10, 20, 40 and 80 min, and spotted on a Whatman filter. Radioactivity was measured using a Beckman scintillation counter.

As a result, when compared to the LysRS protein, the LysRS-PHM fusion protein showed high tRNA synthetase activity (FIG. 13*b*). This result indicates that the LysRS-PHM fusion protein, like the LysRS protein, has an ability to bind to lysine tRNA, and that binding of the LysRS-PHM fusion protein to lysine tRNA increases solubility and refolding efficiency of the target protein.

EXAMPLE 9

RNA-Mediated Protein Folding of LysN-Fused EGFP in Vitro

Because LysRS is large and dimerized protein, it is rather difficult to directly investigate the role of RNA in the folding process. To simplify the system, LysN was used as a single independent RNA-binding protein. LysN was reported to specifically bind to the anticodon of $tRNA^{Lys}$, with dissociation constant ($k_d$) in the range of $10^{-4}$ M, about 10 fold higher than LysRS. The LysN RBD was fused to enhanced green fluorescent protein (EGFP) for monitoring RNA binding-mediated protein folding. To ensure that the chromophore is not formed, the EGFP fusion protein was initially purified as inclusion bodies and used for the refolding studies. The refolding was conducted as follows: The EGFP fusion proteins purified under the denaturation conditions were incubated in 6 M guanidine-HCl and 1 mM DTT for 20 min at 40° C. The denatured proteins were 50 fold diluted into the refolding buffer containing 50 mM MOPS (pH 7.0), 100 mM KCl, 5 mM DTT, 5 mM magnesium acetate, 0.2 mg/ml BSA and indicated RNA. The reaction mixtures were incubated at 30° C. The fluorescence intensity of the refolded EGFP was monitored with excitation at 490 nm and emission at 510 nm using a fluorescence spectrophotometer.

The refolding yield of LysN-EGFP significantly increased by $tRNA^{Lys}$ in a concentration-dependent manner (70% increase in the presence of 12 μM of $tRNA^{Lys}$ compared to its absence), whereas the increase of refolding yield by yeast $tRNA^{Phe}$ was only marginal (less than 10%) (FIGS. 14*a* and 14*b*). The results suggest that refolding enhancement in vitro is dependent on the specific binding between LysN and its cognate tRNA. Consistent with the interpretation, the refolding yield of MBP-EGFP was little affected by $tRNA^{Lys}$ (FIG. 14*a*). These results demonstrate that the binding of $tRNA^{Lys}$ to LysN RBD promotes the folding of downstream EGFP, implying the chaperone activity of $tRNA^{Lys}$ on LysN-EGFP. The results further validate the novel method of using RNA molecule as chaperone for folding and expression of RNA-binding protein-linked target proteins.

EXAMPLE 10

RNA-Mediated Protein Folding In Vivo

To test RNA-mediated protein folding in vivo, we used fusion of C5 protein with EGFP. C5 protein specifically interacts with M1 RNA to form RNase P responsible for the 5'-end processing of *E. coli* tRNAs. M1 RNA component is responsible for the enzyme activity as a prototype ribozyme, where C5 protein plays an auxiliary role for enhancing the RNase activity of M1 RNA. The solubility of C5-EGFP was significantly increased (23% to 78%) when the cognate M1 RNA was coexpressed (FIG. 15*a*). As a control, coexpression of $tRNA^{Lys}$ does not promote the solubility of C5-EGFP (FIG. 15*b*). The low level of soluble expression even without coexpression of M1 RNA is probably due to the endogenous M1 RNA. These results indicate that the folding of downstream EGFP in vivo is greatly stimulated by specific binding of M1 RNA to C5 protein, extending the chaperone function of RNA for protein folding observed in vitro. The in vivo folding studies further validate the rationale of using an RNA molecule as chaperone for expediting folding of target proteins in the present invention.

EXAMPLE 11

The Application of RNA-Mediated Protein Folding for High-Throughput Expression of Mammalian Proteins We examined the efficiency of the RNA-mediated folding vehicle, LysRS, on the expression of target proteins. For this purpose, twenty-seven human proteins potentially related to the progression of gastric or liver cancers and four mouse proteins were tested. The information of test proteins is summarized (Table 2).

TABLE 2

| Tested proteins | | | | |
|---|---|---|---|---|
| No. | Gene symbol | UniGene | RefSeq | Name |
| 1 | ADA | Hs.407135 | NM_000022 | Adenosine deaminase |
| 2 | AGR2 | Hs.530009 | NM_006408 | Anterior gradient 2 homolog (*Xenopus laevis*) |

TABLE 2-continued

Tested proteins

| No. | Gene symbol | UniGene | RefSeq | Name |
|---|---|---|---|---|
| 3 | ANGPTL4 | Hs.9613 | NM_139314 | Angiopoietin-like 4 |
| 4 | AP1M2 | Hs.18894 | NM_005498 | Adaptor-related protein complex 1, mu 2 subunit |
| 5 | ARD1A | Hs.433291 | NM_003491 | ARD1 homolog A, N-acetyltransferase (*S. cerevisiae*) |
| 6 | Ard1 | Mm.305796 | NP_063923 | N-acetyltransferase ARD1 homolog (*S. cerevisiae*) |
| 7 | ARG1 | Hs.440934 | NM_000045 | Arginase, liver |
| 8 | BSG | Hs.501293 | BC009040 | Basigin (OK blood group) |
| 9 | CCT5 | Hs.1600 | NM_012073 | Chaperonin containing TCP1, subunit 5 (epsilon) |
| 10 | CXX1 | Hs.522789 | NM_003928 | CAAX box 1 |
| 11 | CYP1B1 | Hs.154654 | NM_000104 | Cytochrome P450, family 1, subfamily B, polypeptide 1 |
| 12 | E2-EPF | Hs.396393 | NM_014501 | Ubiquitin-conjugating enzyme E2S |
| 13 | FAM3D | Hs.61265 | NM_138805 | Family with sequence similarity 3, member D |
| 14 | GNB2L1 | Hs.5662 | NM_006098 | Guanine nucleotide binding protein (G protein), beta polypeptide 2-like 1 |
| 15 | GPI | Hs.466471 | NM_000175 | Glucose phosphate isomerase |
| 16 | GSTA1 | Hs.446309 | NM_145740 | Glutathione S-transferase A1 |
| 17 | HPR | Hs.512155 | NM_020995 | Haptoglobin-related protein |
| 18 | IFI30 | Hs.14623 | NM_006332 | Interferon, gamma-inducible protein 30 |
| 19 | ILF2 | Hs.75117 | NM_004515 | Interleukin enhancer binding factor 2 |
| 20 | L259 | Mm.89556 | AF534879 | cDNA sequence BC028528 |
| 21 | L259Δ | Mm.89556 | AF534879 | Deletion of L259 from 1st amino acid to 16th amino acid |
| 22 | LECT2 | Hs.512580 | NP_002293 | Leukocyte cell-derived chemotaxin 2 |
| 23 | MIC-1 | Hs.515258 | NP_004855 | Growth differentiation factor 15 |
| 24 | MTSS1 | Hs.336994 | O43312 | Metastasis suppressor 1 |
| 25 | mVDUP1 | Mm.271877 | NP_076208 | Thioredoxin interacting protein |
| 26 | NT5C3 | Hs.487933 | NM_016489 | 5'-nucleotidase, cytosolic III |
| 27 | PTMA | Hs.459927 | NM_002823 | Prothymosin, alpha (gene sequence 28) |
| 28 | PTTG1IP | Hs.474010 | NM_004339 | Pituitary tumor-transforming 1 interacting protein |
| 29 | REG-IV | Hs.171480 | NP_114433 | Regenerating islet-derived family, member 4 |
| 30 | UBD | Hs.44532 | NP_006389 | Ubiquitin D |
| 31 | ZNF9 | Hs.518249 | NM_003418 | Zinc finger protein 9 (a cellular retroviral nucleic acid binding protein) |

These proteins are diverse in location (cytoplasmic, organellar, and extracellular), pI (lowest pI=3.71, PTMA, highest pI=9.52, MIC-1), and molecular weight (lowest MW=12 kDa, PTMA, highest MW=82.3 kDa, MTSS1).

Most proteins were expressed as soluble form at 20-37° C. (FIG. 16) and could be purified via one-step Ni-affinity chromatography. Even in rare cases where the expression level was low (e.g., MTSS1) possibly because of codon bias between *E. coli* host and human or instability of expressed proteins in *E. coli* cytoplasm, the proteins were also expressed as soluble form. After purification of fusion proteins, the target proteins released from the N-terminal RNA binding module by TEV protease remained soluble over prolonged storage at 4° C. (data not shown), possibly indicating proper folding of proteins under fusion context. Consequently, we here provide, based on the RNA-mediated protein folding in the present invention, an extremely robust high-throughput expression platform for mammalian proteins in target host.

EXAMPLE 12

Soluble Expression of Viral Proteins

The influenza virus belongs to negative-strand RNA virus consisting of eight segments of negative-stranded RNAs. Currently, influenza viruses are one of the major pathogens that threaten human health on a global scale. The majority of influenza proteins had been expressed in *E. coli* host as insoluble form. For the development of therapeutic, diagnostic or prophylactic agents against the viruses, the preparation of properly folded soluble proteins is prerequisite. Here we applied LysRS to the expression of the proteins of influenza virus A and B as soluble form.

NA, M1, M2, NS1 and NS2 proteins of influenza virus A were fused to the C-terminus of LysRS. All LysRS-fused proteins were expressed predominantly as soluble form (FIG. 17). The fusion proteins were expressed at 27° C. for 6 h after the treatment of IPTG, except NA at 20° C. for overnight culture. M1, M2, NS1 and NS2 proteins of influenza virus B were also fused to the C-terminus of LysRS. Again, these fusion proteins were expressed almost completely as soluble form (FIG. 18). The fusion proteins were expressed at 27° C. for 6 h after the IPTG induction, except NS1 at 20° C. for overnight culture. The results show that the present invention is useful for soluble expression of variety of viral proteins.

EXAMPLE 13

The Assay of Influenza RNA Polymerase Derived from LysRS Fusion In Vitro

The influenza RNA polymerase, a major target for therapeutic intervention, consists of PA, PB1 and PB2. However, it has not been reported that the functionally active RNA polymerase are successfully reconstituted in vitro from the proteins expressed in *E. coli*. For the reconstitution of RNA polymerase in vitro, PA, PB1, and PB2 of influenza strains such as A/WSN/33 and B/Lee/40 were fused to LysRS, respectively, and the LysRS-fused proteins were expressed in a soluble form (FIGS. 19 and 20, respectively). The purified fusion proteins were pre-treated with TEV protease to release the influenza polymerase components from LysRS, and the cleaved mixtures were used for the reconstitution in vitro.

The results were shown in FIG. 21. vRNA (55mer) were used as a model template. As a positive control, viral core containing native RNA polymerase complexes, derived from the influenza viral particles were used. In this case, the RNA with the expected size was produced. The reconstitution of RNA polymerase components derived from LysRS fusion proteins also produced the RNA with the same size, indicating that the RNA polymerase produced by the present invention are functionally active. The in vitro reconstitution system could be a useful tool for the high-throughput screening of therapeutic agents against influenza viruses.

EXAMPLE 14

Analysis of Effect of Co-Expression of RNA Molecules with Fusion Partners on Solubility of a Target Protein When co-expressing RNA molecules known to bind the fusion partners, effect of such co-expression on solubility of a target protein was evaluated, as follows. A vector expressing lysine tRNA binding to lysRS and a vector expressing a target protein PHM (42-384 amino acid residues of peptidylglycine alpha-monooxygenase) fused with lysRS were prepared. After co-expressing the two vectors, solubility of the fusion protein was analyzed.

First, the vector expressing lysine tRNA was constructed, as follows. tRNA gene was amplified by PCR using genomic DNA from JM109 cells as a template and primers designated SEQ ID NO: 55 and SEQ ID NO: 56. Separately, PCR was carried out using primers designated SEQ ID NO: 57 and SEQ ID NO: 58 to amplify T7 terminator region gene. The amplified tRNA gene and T7 terminator region gene were digested with Sal I/Nco I and Nco I/Sph I, respectively, and then ligated to a pLysE vector (Novagen) digested with SalI/SphI. The resulting vector was designated as "pT7lys-tRNA".

Next, the vector expressing PHM fused to lysRS was constructed, as follows. A gene corresponding to a region ranging from 42 to 384 amino acid residues of rat peptidylglycine α-hydroxylating monooxygenase (PHM; EC 1.14.17.3) was amplified by PCR using pBSkrPHMcc (Prigge et al, *Nat. Struct. Biol.,* 6: 976-983, 1999) as a template and primers designated SEQ ID NO: 59 and SEQ ID NO: 60. The amplified polynucleotide fragments were inserted into BamH I/Hind III sites at the multi cloning site (MCS) of pGE-lysRS vector, and the resulting vector was designated as "plysRS-PHM".

HMS174(DE3) cells were cotransfected with the pT7lys-tRNA vector and plysRS-PHM vector, and the resulting transformant was designated as "HMS174(plysRS-PHM+pT7lys-tRNA)". Separately, HMS174(DE3) cells were cotransfected with the pMBP-PHM vector and pT7lys-tRNA vector, and the resulting transformant was designated as "HMS174(pMBP-PHM+pT7lys-tRNA)", which was used as a control. After incubating the transformants HMS174 (plysRS-PHM+pT7lys-tRNA) and HMS174(pMBP-PHM+pT7lys-tRNA) at 37° C. and 30° C., respectively, protein expression was induced according to the same method as in Example 1, and then solubility of fusion proteins was evaluated. Herein, because MBP-PHM fusion protein was found to be mainly expressed in an insoluble form at 37° C., to provide an expression environment similar to that of LysRS-PHM, the MBP-PHM fusion protein was expressed at 30° C. Also, HMS174(pMBP-PHM) and HMS174(pMBP-PHM) transformants were used as negative controls, which were not cotransfected with the pT7lys-tRNA vector.

As a result, when being co-expressed with lys-tRNA, LysRS-PHM fusion protein was found to have 10% higher solubility than when expressed without co-expression of lys-tRNA, while MPB-PHM fusion protein showed similar solubility when expressed with or without co-expression of lys-tRNA (FIG. 22). These results indicate that the lysine tRNA increases solubility of target protein by specifically binding to the LysRS RBD, confirming the novel chaperone method by RNA molecule which constitutes the embodiment of the present.

INDUSTRIAL APPLICABILITY

As described hereinbefore, an RNA molecule, either artificially introduced or resident in the host cell, exerts folding and enhancing the solubility of RNA-binding protein-linked target protein. The novel process of protein folding is extremely robust for soluble expression of variety of proteins from various origins leading to better quality and increased productivity of target proteins. The present invention is useful for high-throughput expression of variety of proteins for therapeutic, prophylactic and diagnostic applications. The method is useful for various disciplines of post-genome R&D activities including structure-function analysis of proteins, functional validation of new drug target for expediting development of new small drug entities, development of new protein drugs and development of high quality protein chip.

What is claimed is:

1. A method for improving the folding efficiency and solubility of a target protein covalently linked to an RNA-binding protein comprising:

reacting an RNA molecule as a molecular chaperone with a target protein covalently linked to an RNA-binding protein, wherein the RNA-binding protein is selected from the group consisting of Lysyl-tRNA synthetase, C5 protein of ribonuclease P, Ffh protein of signal recognition particle, NP protein of influenza virus, ribosomal S1 protein, ribosomal S4 protein, ribosomal S17 protein, DbpA, Hsp15, DnaK, and murine Hsc70; and the RNA molecule binds to the RNA-binding protein.

2. The method according to claim 1, wherein the RNA molecule is selected from the group consisting of mRNA, tRNA, rRNA, nuclear RNA, non-coding RNA, viral RNA and ribo-polynucleotides prepared by genetic recombination techniques.

3. The method according to claim 1, wherein the RNA molecule is naturally present in cells, or artificially introduced by co-expression.

4. The method according to claim 3, wherein the RNA molecule is artificially over-expressed by constructing a vector expressing said RNA molecule and then introducing the vector into a host cell.

5. The method according to claim 4, wherein the method comprises the steps of:

1) constructing an expression vector encoding a fusion protein in which the target protein is linked to an RNA-binding protein;

2) constructing an expression vector expressing an RNA molecule capable of binding to the RNA-binding protein linked to the target protein; and 3) cotransforming a host cell with the expression vectors prepared in steps 1 and 2.

6. The method according to claim 5, wherein the host cell is *E. coli, B. sublitis, S. serevisiae, S. pombe, H polymorpha, P. pastoris*, an insect cell, a plant cell or a mammalian cell.

7. A method for producing a target protein having improved solubility and folding efficiency using an RNA molecule as a molecular chaperone, comprising expressing a target protein covalently linked to an RNA-binding protein, and forming a ribonucleotide protein (RNP) complex between an RNA molecule and the RNA-binding protein, wherein the RNA-binding protein is selected from the group consisting of lysyl-tRNA synthetase, C5 protein of ribonuclease P, Ffh protein of signal recognition particle, NP protein of influenza virus, ribosomal S1 protein, ribosomal S4 protein, ribosomal S17 protein, DbpA, Hsp15, DnaK, and murine Hsc70; and the RNA molecule binds to the RNA-binding protein.

8. The method according to claim 7, wherein the RNA molecule is selected from the group consisting of mRNA, tRNA, rRNA, nuclear RNA, non-coding RNA, viral RNA and ribo-polynucleotides prepared by genetic recombination techniques.

9. The method according to claim 7, wherein the RNA molecule is naturally present in cells, or artificially co-expressed.

10. The method according to claim 7, wherein the RNA molecule is artificially over-expressed by constructing a vector expressing said RNA molecule and then introducing the vector into a host cell.

11. The method according to claim 7, wherein the method comprises the steps of:

1) constructing an expression vector encoding a fusion protein in which the target protein is covalently linked to the RNA-binding protein;

2) constructing an expression vector expressing an RNA molecule capable of binding to the RNA-binding protein linked to the target protein; and 3) cotransforming a host cell with the expression vectors prepared in steps 1 and 2.

* * * * *